US008862229B2

(12) United States Patent
Stahmann

(10) Patent No.: US 8,862,229 B2
(45) Date of Patent: Oct. 14, 2014

(54) SYSTEM AND METHOD FOR MONITORING CARDIOVASCULAR PRESSURE

(75) Inventor: Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 711 days.

(21) Appl. No.: 12/793,106

(22) Filed: Jun. 3, 2010

(65) Prior Publication Data

US 2010/0312301 A1 Dec. 9, 2010

Related U.S. Application Data

(60) Provisional application No. 61/183,794, filed on Jun. 3, 2009.

(51) Int. Cl.
| | |
|---|---|
| *A61N 1/00* | (2006.01) |
| *A61B 5/04* | (2006.01) |
| *A61B 5/0215* | (2006.01) |
| *A61N 1/365* | (2006.01) |
| *A61B 5/022* | (2006.01) |
| *A61B 5/00* | (2006.01) |

(52) U.S. Cl.
CPC ............. *A61B 5/0215* (2013.01); *A61B 5/022* (2013.01); *A61N 1/36564* (2013.01); *A61B 5/7264* (2013.01); *A61B 5/02158* (2013.01)
USPC ............................................ 607/17; 600/523

(58) Field of Classification Search
CPC .... A61B 5/0215; A61B 5/022; A61B 5/7264; A61B 5/02158; A61N 1/36564
USPC ........................................... 600/523; 607/17
See application file for complete search history.

(56) References Cited

U.S. PATENT DOCUMENTS

| 5,312,446 A | 5/1994 | Holschbach et al. |
| 5,313,953 A | 5/1994 | Yomtov et al. |

(Continued)

FOREIGN PATENT DOCUMENTS

| WO | WO-89/09514 | 10/1989 |
| WO | WO-2009025734 A1 | 2/2009 |

OTHER PUBLICATIONS

International Search Report, from corresponding application PCT/US2010/037193, mailed Sep. 14, 2010, 15 pages.
Auricchio, Angelo et al., "Effect of Pacing Chamber and Atrioventricular Delay on Acute Systolic Function of Paced Patients with Congestive Heart Failure," *Circulation 99*, 1999, 2993-3001.

(Continued)

*Primary Examiner* — Catherine Voorhees
(74) *Attorney, Agent, or Firm* — Pauly, DeVries Smith & Deffner, LLC

(57) ABSTRACT

A method for modulating one or more functions of an implanted medical device is disclosed. The method includes measuring a cardiovascular pressure of a patient; evaluating the cardiovascular pressure based on one or more characteristics of a cardiac cycle of the patient at the time the pressure was measured; and modulating one or more functions of the device based on the pressure. Also disclosed is a method for assessing a cardiovascular pressure of a patient with an implanted medical device that includes detecting one or more characteristics of a cardiac cycle of the patient's heart; detecting the cardiovascular pressure of the patient; classifying the cardiovascular pressure based on one or more characteristics of the cardiac cycle of the patient's heart; and displaying the cardiovascular pressure along with the classification. Also disclosed is a system for collection and display of a cardiovascular pressure of a patient.

16 Claims, 13 Drawing Sheets

(56) References Cited

U.S. PATENT DOCUMENTS

| | | | |
|---|---|---|---|
| 5,404,877 | A | 4/1995 | Nolan et al. |
| 5,411,031 | A | 5/1995 | Yomtov |
| 5,830,150 | A * | 11/1998 | Palmer et al. ............ 600/523 |
| 6,045,513 | A | 4/2000 | Stone et al. |
| 6,090,047 | A | 7/2000 | Kass et al. |
| 6,580,946 | B2 | 6/2003 | Struble |
| 6,821,256 | B2 | 11/2004 | Ackerman et al. |
| 6,865,419 | B2 | 3/2005 | Mulligan et al. |
| 6,969,369 | B2 | 11/2005 | Struble |
| 6,974,413 | B2 | 12/2005 | Bardy |
| 7,162,301 | B2 | 1/2007 | Kim et al. |
| 7,188,151 | B2 | 3/2007 | Kumar et al. |
| 7,297,108 | B2 | 11/2007 | Iliff |
| 7,433,827 | B2 | 10/2008 | Rosenfeld et al. |
| 7,483,743 | B2 | 1/2009 | Mann et al. |
| 2006/0041281 | A1 | 2/2006 | Von Arx et al. |
| 2006/0264771 | A1 * | 11/2006 | Lin et al. ............ 600/513 |
| 2008/0195165 | A1 | 8/2008 | Stahmann et al. |
| 2008/0275520 | A1 | 11/2008 | Hopper et al. |
| 2008/0288013 | A1 | 11/2008 | Schecter |
| 2010/0030086 | A1 * | 2/2010 | Zielinski et al. ......... 600/485 |
| 2010/0030302 | A1 * | 2/2010 | Blowers et al. ......... 607/60 |

OTHER PUBLICATIONS

Bernstein, Alan D. et al., "The Revised NAPSE/BPEG Generic Code for Antibradycardia, Adaptive-Rate, and Multisite Pacing," *Journal of Pacing and Clinical Electrophysiology*, vol. 25, No. 2, Feb. 2002, 260-263.

Braunschweig, Frieder et al., "Optimization of the AV Delay in Cardiac Resynchronization Therapy Using an Implanted Hemodynamic Monitor," *Eurospace Supplements*, vol. 7, May 2005, 291.

CardioMem CM 3000 Digital Recorder, *The Physician's Resource for Medical Equipment, Inc.*, http://www.physiciansresource,net/2250.html, downloaded Mar. 4, 2009, 1 page.

Cardio Mem CM 3000 Digital Recorder for Holter ECG, getemed / GE Healthcare technical brochure, 2009, 1 page.

CardioMem CM 3000, GE Healthcare / getemed brochure, 2009, 1 page.

Ellengoben, K. et al, *Cardiac Pacing*, Third Edition, 2002, Blackwell Science, Inc., pp. 130 and 141.

Hoppe, Uta C. et al., "Noninvasive pulmonary artery pressure monitoring in patients with heart failure by the RemonCHF device: First multicenter experience," PowerPoint Presentation, dated Sep. 5, 2007, 34 pages.

* cited by examiner

| Parameter | Av* | V* | N | p+ |
|---|---|---|---|---|
| RA mean (mmHg) | 6.0 ± 0.6 | 8.1 ± 0.6 | 22 | <.001 |
| PA systolic (mmHg) | 24.5 ± 1.6 | 28.3 ± 1.7 | 23 | <.001 |
| PA diastolic (mmHg) | 12.6 ± 1.0 | 14.3 ± 1.1 | 23 | <.02 |
| PA mean (mmHg) | 17.1 ± 1.1 | 20.6 ± 1.2 | 23 | <.001 |
| PCW mean (mmHg) | 7.7 ± 1.0 | 13.4 ± 1.2 | 22 | <.001 |
| LV systolic (mmHg) | 141.3 ± 5.2 | 132.0 ± 5.1 | 23 | <.01 |
| LV end-diastolic (mmHg) | 9.8 ± 1.4 | 10.1 ± 0.8 | 22 | NS |
| FA systolic (mmHg) | 141.4 ± 5.1 | 133.4 ± 5.1 | 23 | <.01 |
| FA diastolic (mmHg) | 80.3 ± 2.0 | 80.9 ± 2.4 | 23 | NS |
| FA mean (mmHg) | 105.6 ± 2.8 | 103.1 ± 3.4 | 23 | NS |
| CI.TD (L/min/m$^2$) | 2.575 ± .0148 | 2.073 ± 0.126 | 23 | <.001 |
| CI.Angio (L/min/m$^2$) | 3.337 ± 0.210 | 2.878 ± 0.157 | 19 | <.001 |
| LV.EDVI (mL/m$^2$) | 85.7 ± 7.4 | 76.6 ± 6.8 | 19 | <.001 |
| LV.ESVI (mL/m$^2$) | 46.2 ± 5.9 | 42.2 ± 5.4 | 19 | <.05 |
| LV.SVI (mL/m$^2$) | 39.7 ± 2.6 | 34.3 ± 2.0 | 19 | <.001 |
| LV.EF (%) | 48.9 ± 2.8 | 47.6 ± 2.8 | 19 | NS |
| SVR (dyne-sec-cm$^{-5}$) | 1856.1 ± 160.3 | 2178.0 ± 180.6 | 23 | <.001 |
| PVR (dyne-sec-cm$^{-5}$) | 169.0 ± 16.3 | 152.1 ± 15.0 | 22 | NS |

* Mean ± SEM
+ Paired $t$ test
Angio = angiography; CI = cardiac index; EDVI = end-diastolic volume index; EF = ejection fraction; ESVI = end-systolic volume index; FA = femoral artery; LV = left ventricle; NS = not statistically significant; PA = pulmonary artery; PCW = pulmonary capillary wedge; PVR = pulmonary vascular resistance; RA = right atrium; SVI = stroke volume index; SVR = systemic vascular resistance; TD = thermodilution

FIG. 13

| AV Interval Programming | Change in PAD [mm Hg] | p-value (Mann Whitney U Test) |
|---|---|---|
| AV opt - 60 ms | +2.3 ± 2.3 | <0.001 |
| AV opt - 40 ms | +0.9 ± 2.2 | 0.009 |
| AV opt - 20 ms | +0.3 ± 1.9 | n.s. |
| AV opt + 20 ms | -0.7 ± 1.4 | <0.01 |
| AV opt + 40 ms | +1.0 ± 3.6 | n.s. |
| AV opt + 60 ms | +0.3 ± 1.6 | n.s. |

FIG. 14

SYSTEM AND METHOD FOR MONITORING CARDIOVASCULAR PRESSURE

RELATED APPLICATIONS

This application claims the benefit of U.S. Provisional Application No. 61/183,794 filed Jun. 3, 2009, the contents of which are herein incorporated by reference.

FIELD OF THE INVENTION

Described herein are methods and systems for treating a patient with an implanted medical device. In particular, systems and methods suitable for use with cardiovascular therapies are disclosed.

BACKGROUND

Cardiac rhythm management refers to the treatment and management of cardiac rhythm disorders. In many instances, cardiac rhythm management involves the implantation of medical devices such as a pacemaker and/or implantable cardioverter-defibrillator. These devices typically include circuitry to sense electrical signals from the heart and a pulse generator to provide electrical pulses to stimulate the heart tissue adjacent to the electrodes to produce a contraction of the tissue.

In general, the goal of cardiac rhythm management is to improve the patient's quality of life, morbidity, and mortality by electrical correction of pulse and conduction defects in the heart to simulate a natural, inherent electrical function of the heart and to satisfy the patient's needs while reducing side effects.

SUMMARY OF THE INVENTION

Disclosed herein is a method for modulating one or more functions of an implanted medical device. In one embodiment, the method includes steps of measuring a cardiovascular pressure of a patient; evaluating the cardiovascular pressure based on one or more characteristics of a cardiac cycle of the patient at the time the intravascular pressure was measured; and modulating one or more functions of the implanted medical device based on the cardiovascular pressure. In one embodiment, the implanted medical device is capable of providing an applied electrical stimulus to the patient's heart. In one embodiment, modulating includes one or more of decreasing, increasing, stopping and starting one or more functions of an implanted medical device. In one embodiment, modulating one or more functions includes modulating a cardiac pacing parameter. In one embodiment, cardiovascular pressure includes intravascular pressure. In another embodiment, cardiovascular pressure includes intracardiac pressure. In yet another embodiment, cardiovascular pressure includes pulmonary artery pressure.

Also disclosed herein is a method for assessing a cardiovascular pressure of a patient with an implanted medical device capable of providing an applied electrical stimulus to the patient's heart. The method includes steps of detecting one or more characteristics of a cardiac cycle of the patient's heart; detecting the cardiovascular pressure of the patient; classifying the cardiovascular pressure based on one or more characteristics of a cardiac cycle of the patient's heart at the time the pressure is detected; and displaying the cardiovascular pressure along with the classification. In one embodiment, the method includes a step of modulating programming of cardiac pacing therapy based on the cardiovascular pressure.

Also disclosed herein is a system for collection and display of a cardiovascular pressure of a patient, which includes a sensor capable of generating a first signal indicative of a characteristic of a cardiac cycle of the patient's heart; one or more pressure sensors capable of generating a second signal indicative of a cardiovascular pressure of the patient; one or more transmitters configured to transmit the first and second signal to a database capable of storing patient information in the form of cardiac cycle data and pressure data; a processor configured classify the cardiovascular pressure based on the cardiac cycle data; and a display showing the classification of the cardiovascular pressure. In one embodiment, the cardiac cycle sensor is implanted within the patient. In another embodiment, one or more cardiac cycle sensors are located external to the patient. In one embodiment, one or more cardiovascular pressure sensors are implanted within the patient. In another embodiment, one or more cardiovascular pressure sensors are located external to the patient.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE DRAWINGS

FIG. 13 is a table showing the hemodynamic effects of ventricular and atrioventricular pacing demonstrating that both the diastolic and systolic pulmonary artery (PA) pressures are significantly affected by the type of pacing.

FIG. 14 is a table showing the acute influence of change in atrioventricular (AV) interval on diastolic pulmonary artery (PA) pressure.

DETAILED DESCRIPTION

Figure 1:
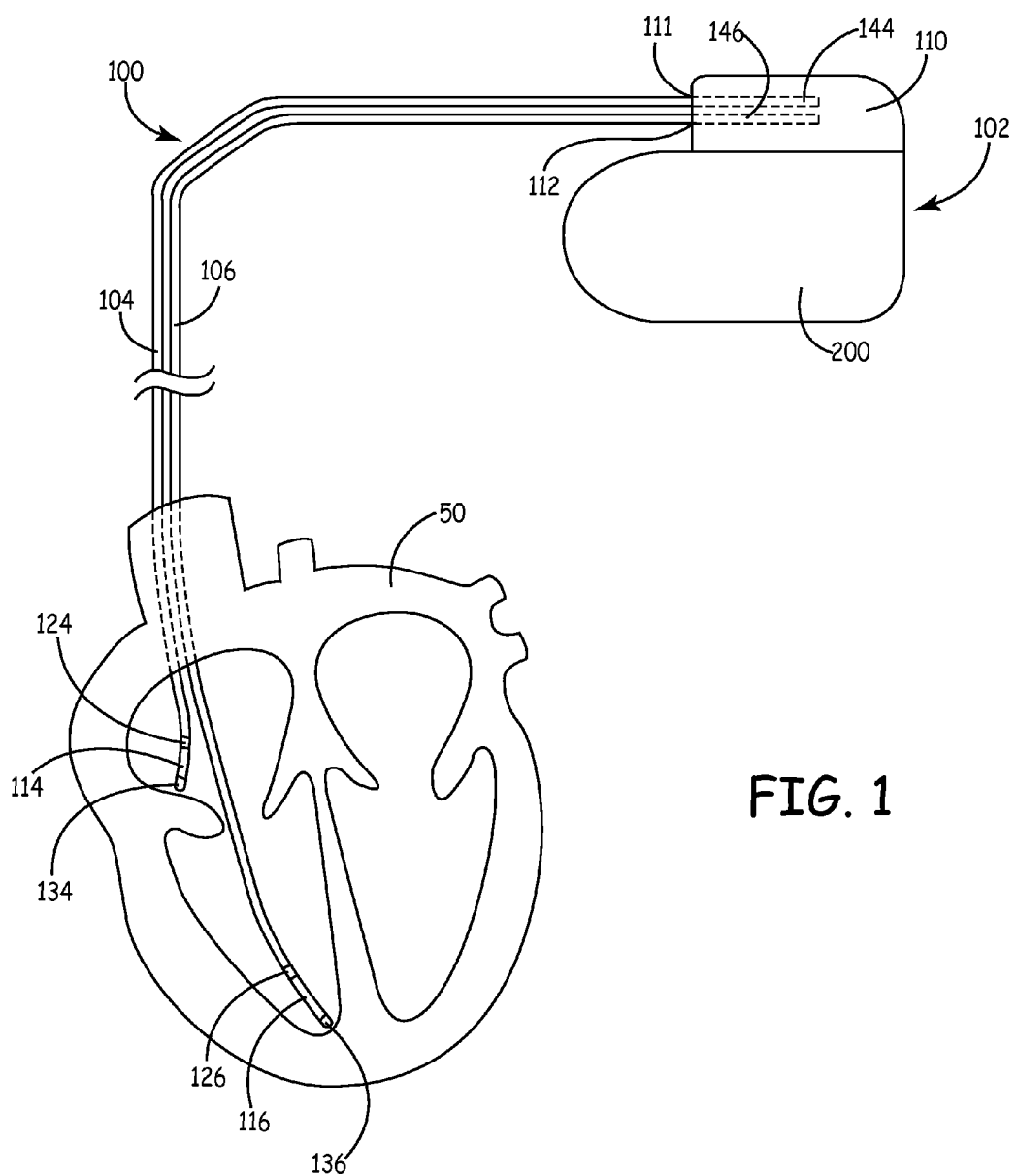
FIG. 1 is a schematic of an implanted medical device as described herein shown in conjunction with a heart.

Cardiovascular pressure can be used as an indicator of cardiovascular health and as a gauge for assessing the efficacy of cardiac therapy. For example, pulmonary artery pressure, including diastolic pulmonary artery pressure can be used as an indicator of cardiovascular health and can provide a general indication of the left ventricular filling pressure and the work load of the right ventricle. Since abnormal cardiovascular pressures are often a consequence of end-stage cardiomyopathy and valvular heart disease, cardiovascular pressure can be used, for example, to diagnose and monitor heart failure status or decompensation of a patient. As used herein, the term "heart failure" refers to a condition in which the heart is unable to ensure adequate circulation. Further, the term "decompensation" refers to an acute exacerbation of heart failure. In general, decompensation is associated with dyspnea, venous engorgement, cyanosis and edema.

Although cardiovascular pressure can vary depending upon the presence and type of applied electrical stimulation during a cardiac cycle, physicians do not typically measure cardiovascular pressure in connection with cardiac resynchronization therapy (CRT). Instead, the physician will generally evaluate a patient's symptoms to monitor decompensation. Furthermore, a physician will typically determine a course of therapy for a patient based on the patient's condition during an admission or office visit. However, evaluating a patient's condition only during admission or an office visit, regardless of the frequency of the visits, typically does not recognize changes in the patient's condition between visits. These changes may indicate a need for a change in therapy. However, if the changes are not recognized during an office visit, the therapy can not be modified to address them. Furthermore, although the use of markers to identify various pacing events is known, current cardiac disease monitoring and management systems do not separate pressure readings by the existence and type of cardiac pacing.

Disclosed herein is a system and method to monitor a patient's condition, such that the patient's therapy can be modified as necessary as a function of the patient's condition. In particular, a method and system are described herein to separate, label and/or otherwise process and/or identify cardiovascular pressure readings according to one or more characteristics of a cardiac cycle in a patient. For example, cardiovascular pressure readings can be classified based on the existence and type of cardiac pacing. In particular, devices and systems for incorporating cardiovascular pressure measurement in connection with cardiac rhythm management (CRM) systems are provided. In general, Cardiac Rhythm Management (CRM) systems stimulate cardiac tissue by applying an electrical stimulus, thereby producing a contraction of the tissue.

Implantable devices used to treat, monitor or diagnose diseases or conditions are referred herein as implantable medical devices (IMDs). Implantable medical devices can be used to treat irregular heartbeats, known as arrhythmias. Many types of implantable medical devices exist and include, but are not limited to: pacemakers, generally used to manage bradycardia, an abnormally slow or irregular heartbeat; implantable cardioverter defibrillators (ICDs), generally used to treat tachycardia, heart rhythms that are abnormally fast and life threatening; cardiac resynchronization therapy (CRT) devices, generally used to resynchronize ventricular wall motion; and implantable cardiovascular monitors and therapeutic devices, including cardiac devices that include or work in coordination with one or more neuro-stimulating devices, drugs, drug delivery systems, or other therapies that are used to monitor and treat problems of the heart, including structural problems and rhythm problems, for example, those associated with congestive heart failure. Various types of pacemakers, implantable cardiac defibrillators, cardiac resynchronization therapy devices and implantable cardiovascular monitors and devices are known and are suitable for use with the method and system described herein. Examples of other therapies used for the treatment of heart failure include, but are not limited to, post-myocardial infarction (post-MI) pacing therapy, neuro-cardiac therapy, and intermittent pacing therapy.

Current generation pacemakers, implantable defibrillators/cardioverters and cardiac resynchronization therapy devices have the ability to store different types of information in order to provide feedback to the physician about the patient and/or system. Examples of typical stored information includes, but is not limited to: administrative data, for example, model, serial number, patient name, date of implantation, and indication for implantation; programmed data, for example, mode, rate, refractory period, hysteresis, pulse amplitude, pulse width and sensitivity; measured data, for example, rate, pulse amplitude, pulse current, pulse energy, pulse charge, lead impedance, battery impedance, battery voltage, and battery current drain; and other stored data, for example, Holter function, and rhythm histogram.

Such information is useful not only in device programming but also in the management of the patient's arrhythmias and other conditions. Current implantable devices with large memories and sensors can be used to produce a set of data that indicates patient functional status on an on-going basis. In addition, a well-documented set of derived measures can be determined based on the collected measures, as is known in the art. As described herein, this information, including information relating to the type and existence of pacing, collected by the system, can be used to asses the quality of the therapy, and if necessary, to modulate one or more functions of the implanted medical device.

In many presently available devices, stored device information can be retrieved using a proprietary interrogator or programmer. Sequential logging and analysis of interrogations can provide an opportunity for recognizing changes in patient condition. In one embodiment, patient information is continuously monitored. In another embodiment, the data is gathered periodically, for example, hourly or daily. In another embodiment, the data is gathered opportunistically, for example, when relevant data is collected for other purposes, it can be stored and analyzed according to the methods described herein. In another embodiment, the data is collected on command or based on an instruction. In yet another embodiment, the data is collected based on a detected event or symptom. In yet another embodiment, the data is generated by experimenting with various treatment parameters to develop a database.

One embodiment provides a method and system for modulating one or more functions of an implanted medical device based on measurements of a cardiovascular pressure of a patient. In one embodiment, the cardiovascular pressure is characterized or classified based on one or more characteristics of a cardiac cycle of the patient. In one embodiment, the cardiovascular pressure is characterized based on whether or not the patient's heart was paced at the time the pressure was measured. As used herein, the term "cardiac pacing" refers to the regulation of contraction of the heart muscle by the application of electrical stimulation pulses or shocks. As used herein, the term "cardiovascular pressure" includes both intravascular pressure (e.g. pulmonary artery pressure) and intracardiac pressure (e.g. right ventricular pressure). As used herein, the term pressure includes, for example, diastolic pressure, systolic pressure, mean pressure, pulse pressure and pressure transients (e.g. dP/dt). The term modulating can refer to decreasing, increasing, stopping and/or starting one or more functions of an implantable medical device.

Another embodiment provides a method for assessing cardiovascular pressure of a patient, in which the patient has an implanted medical device capable of providing an applied electrical stimulus to the patient's heart. In one embodiment, a first parameter indicative of a characteristic or element of a cardiac cycle is detected and a first set of data indicative of this characteristic or element of the cardiac cycle is generated. A second parameter indicative of the cardiovascular pressure of the patient can likewise be detected and a second set of data indicative of the cardiovascular pressure generated. The pressure data is then classified based on one or more characteristics of the cardiac cycle at the time the pressure is detected. The pressure data can then be displayed along with the classification. In one embodiment, the programming and/or delivery of cardiac pacing therapy is modulated based on the pressure data.

The systems and methods disclosed herein can be incorporated into devices that detect, display and/or process cardiac cycle and/or cardiovascular pressure data. Suitable devices include stand alone systems and integrated systems. As used herein, the term "stand alone" system refers to a system that is not integrated with an implantable medical device and is capable of being operated independently of the implantable medical device. For example, a cardiac cycle sensing system and/or cardiovascular pressure sensing system may not be integrated with a pacemaker. Instead, the cardiac cycle sensing system and/or the cardiovascular pressure sensing system may determine the type and/or existence of cardiac pacing or cardiovascular pressure by the addition of a suitable independently operated sensor. As used herein, the term "integrated system" refers to a system that is not configured for use independent of the implantable medical device. In one embodiment, one or more elements of the "integrated system" are included within or physically attached to the implantable medical device. For example, the operational circuitry of the "integrated system" may be included within the implantable medical device. For example, detection or identification of cardiac pacing or cardiovascular pressure may be accomplished using a system in which the cardiac cycle and/or cardiovascular pressure sensing system(s) are integrated with a pacemaker, wherein the system uses information the pacemaker collects regarding the type and existence of pacing or cardiovascular pressure. In another embodiment two or more elements of the "integrated system" are communicatively coupled. For example, an implanted pressure sensor may communicate with an implanted ICD via a wireless radio frequency or acoustic communication pathway.

The system can include implanted or internal devices, external devices, or both. The external and/or internal devices can be integrated and/or stand alone devices. In one embodiment, the system includes one or more external devices, including external pacemakers, external cardioverter-defibrillators, and external resynchronization devices. Additional examples of external devices that monitor cardiac activity include ambulatory electrocardiography devices or Holter monitors, which typically continuously monitor electrical activity of the heart for 24 hours or more.

Cardiac Cycle

In one embodiment, a first parameter indicative of a characteristic or element of a cardiac cycle type is detected and a first set of data indicative of this characteristic or element of the cardiac cycle is generated. As used herein, the term "cardiac cycle" refers to the sequence of events between the start of one contraction of the heart's ventricles and the start of the next contraction of the heart's ventricles. A ventricular pacing pulse initiating a contraction of the heart's ventricles is generally considered to be part of the cardiac cycle in that it contains the ventricular contraction initiated by the pacing pulse. In general, a cardiac cycle includes stages of systole, diastole, and an intervening pause. Electrocardiography (ECG or EKG) refers to a recording of the electrical activity of the heart over time. A typical electrocardiogram tracing of a cardiac cycle includes a P wave, a QRS complex and a T wave. The P wave reflects atrial depolarization. The QRS complex corresponds to the depolarization of the ventricles. Although not every QRS complex contains a Q wave, an R wave, and an S wave, by convention, any combination of these waves can be referred to as a QRS complex. The duration, amplitude, and morphology of the QRS complex is useful in diagnosing cardiac arrhythmias, conduction abnormalities, ventricular hypertrophy, myocardial infarction, electrolyte derangements, and other disease states.

In one embodiment, cardiac cycle information can be obtained using "stand alone" external or surface electrodes, placed on one or more parts of the body to detect electrical impulses. In another embodiment, cardiac cycle information can be obtained using an implanted system, for example, a system that is "integrated" with an implantable medical device.

As used herein, the term "characteristic" or "element" of a cardiac cycle refers to a detectable parameter of the cardiac cycle. A characteristic of a cardiac cycle may be intrinsic or due to the application of one or more therapies. As used herein, the term "intrinsic" refers to the spontaneous cardiac activity through the normal electrical pathways. Applied therapies can include electrical stimulation therapy, including but not limited to cardiac, neuro and/or direct organ (e.g. kidney) electrical stimulation therapy. Examples of characteristics or elements of a cardiac cycle, include, but are not limited to: whether the cardiac cycle is an intrinsic cycle or an evoked cycle, whether or not the cardiac cycle is paced, which chamber or chambers were paced, the pacing site or sites within a chamber, the pacing mode or rate, the pacing waveform (e.g. pulse duration, pulse width, monophasic/biphasic), atrioventricular (AV) interval, biventricular delay, and refractory period. A further example is the presence, absence, dose and/or duration of neuro and/or direct organ electrical stimulation therapy. Various characteristics or elements of a cardiac cycle can be detected and used in connection with the methods and systems described herein.

Cardiovascular Pressure Sensor

Cardiovascular pressure can provide an overall reflection of the functioning of a patient's heart and circulatory system.

The cardiovascular pressure in a patient's arterial system can be represented by the peak systolic and diastolic levels of the pressure pulse.

Cardiovascular pressure can be measured directly or indirectly. The most common method for measuring cardiovascular pressure indirectly is with a sphygmomanometer and stethoscope. The primary benefits of the sphygmomanometer and stethoscope procedure are that it is simple for the medical practitioner to use, is non-invasive and is relatively inexpensive. The primary drawbacks of the use of the sphygmomanometer and stethoscope procedure reside in the limited amount of data that it provides, and the relative inaccuracy of the procedure.

Another method for measuring cardiovascular pressure is by a direct measurement. In one embodiment, a needle or catheter is inserted into an artery of the patient, for example, the brachial, radial, or femoral artery to obtain a direct hemodynamic measurement. The catheter is typically connected to a pressure sensitive device or a strain-gauge transducer. The mechanical energy that the blood exerts on the transducer's recording membrane is converted into changes in electrical voltage or current that can be calibrated in millimeters of mercury. The electrical signal can then be transmitted to an electronic recorder and a display device, which continually records and displays the pressure waves. One example of an implantable hemodynamic pressure monitor is the Remon ImPressure™ device (Boston Scientific Corporation, Natick, Mass.). The Remon ImPressure™ device includes an implant with a wireless sensor that can communicate with implanted device. In one embodiment, pulmonary artery (PA) pressure is measured by right heart catheterization, for example, using a pulmonary artery catheter or arterial line catheter. In another embodiment, pulmonary artery (PA) pressure is assessed by pulsed Doppler echocardiography. In another embodiment cardiovascular pressure is assessed via a pressure sensor inserted into, and held within, the body via a catheter. Two examples of catheter-based pressure sensors are the Swan-Ganz VIP catheter (Edwards Lifesciences, Irvine, Calif.) and the Mikro-Tip pressure transducer catheter (Millar Instruments, Houston, Tex.).

In one embodiment, the system or implantable medical device includes one or more hemodynamic sensors. The hemodynamic sensor can be configured to monitor one or more of many known cardiovascular parameter values, including, but not limited to an end expiratory diastolic value (EED), end expiratory systolic pressure, systolic time interval, a rate of change of cardiovascular pressure (dP/dt), pulmonary artery (PA) pulse pressure, heart rate, or a central tendency of the cardiovascular pressure such as the mean cardiovascular pressure. In general, a mean cardiovascular pressure is an arithmetic average of the pressure during one cardiac cycle, for example, the time between the start of one contraction of the heart and the start of the next. To simplify calulation common formula used to determine mean systemic pressure is (⅔ diastolic+⅓ systolic)/3. In one embodiment, the hemodynamic sensor is a cardiovascular sensor. In another embodiment, the cardiovascular sensor is configured to detect an intravascular pressure. In another embodiment, the sensor is configured to detect an intracardiac pressure. In another embodiment, the sensor is configured to detect a pulmonary artery pressure.

In one embodiment, the pressure sensor is implanted within an artery of a patient. In one embodiment, the pressure sensor is implanted within a pulmonary artery of a patient. In one embodiment, the pressure sensor is implanted within a main pulmonary artery. In another embodiment, the pressure sensor is implanted within the left and/or right pulmonary arteries. In one embodiment, the sensor is designed to generate a signal that is indicative of a cardiovascular pressure and configured to transmit the signal to an implantable medical device, an external device, or both.

In one embodiment, the cardiovascular pressure sensor is integrated with an implantable medical device. For example, the distal end of one or more leads of an implantable medical device can incorporate a pressure transducer for producing electrical signals representative of the patient's cardiovascular pressure. In one embodiment, the electrical stimulus and the sensor signal are transmitted through the same lead. In another embodiment, more than one lead is provided and the electrical stimulus and the sensor signal are transmitted through different leads. In another embodiment, a pressure sensor is used that includes telemetry circuitry to allow the sensor to communicate with the implantable medical device, an external unit, or both. In yet another embodiment, the cardiovascular pressure can be monitored by a distally or externally located sensor, for example, by radio frequency (RF) signals or acoustic signals.

Pressure Classification

Cardiovascular pressure can vary depending upon the presence and type of cardiac pacing. For example, FIGS. 4 and 6 (Ellenbogen K, Wood M, Cardiac Pacing, Third Edition, 2002, Blackwell Science, Inc., pages 130 and 141) and FIGS. 7 and 8 (Auricchio et al., "Effect of pacing chamber and atrioventricular delay on acute systolic function of paced patients with congestive heart failure," Circulation (1999), 99(23):2993-3001) demonstrate the effect of pacing on systemic blood pressure. FIGS. 5, 6, and 13 (Ellenbogen, supra) and FIG. 14 (Braunschweig et al., "Optimization of the AV delay in cardiac resynchronization therapy using implanted hemodynamic monitor," Europace (2005), 7(3):291) demonstrate that PA pressures are acutely affected by pacing.

Figure 4:
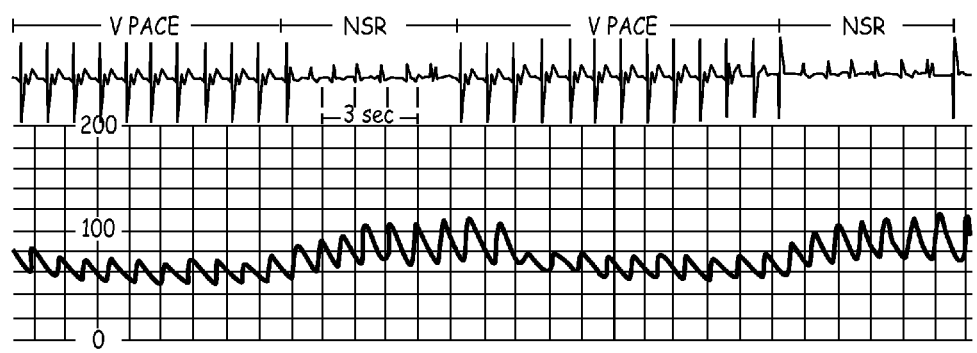
FIG. 4 is a graph showing the effect of ventricular pacing on radial artery cardiovascular pressure.
Figure 5:
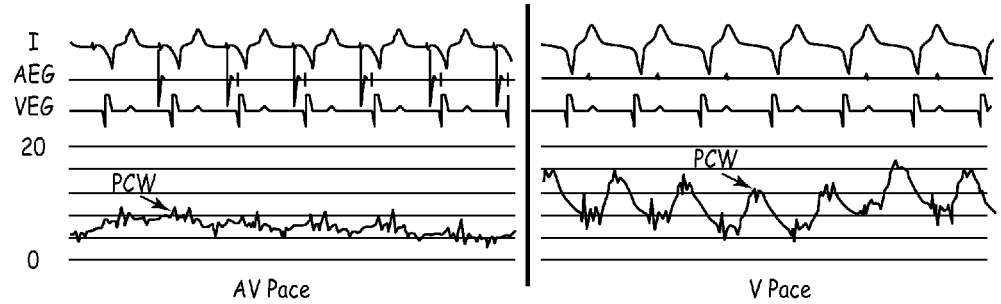
FIG. 5 is a graph showing the effect of ventricular and atrioventricular pacing on pulmonary capillary wedge (PCW) pressure.
Figure 6B:
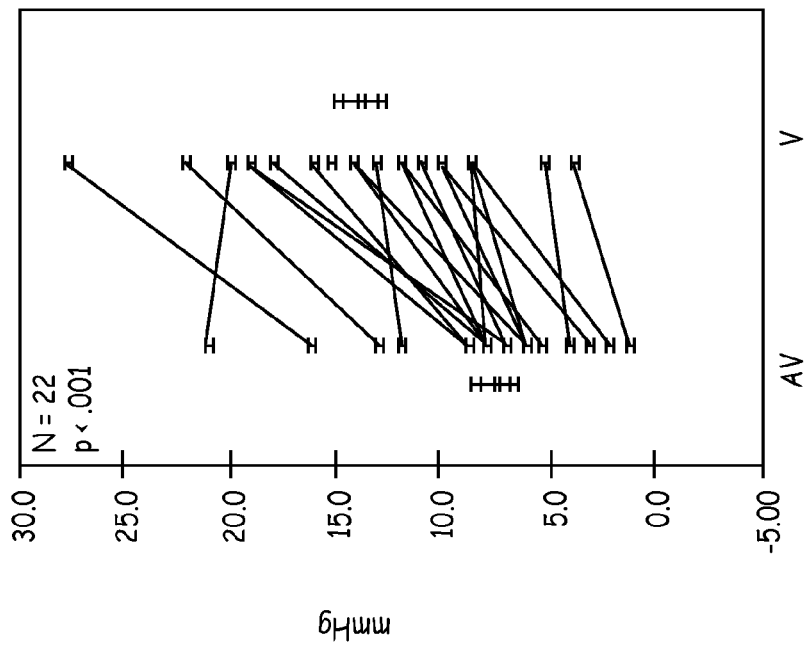
FIGS. 6A and B are graphs showing the effect of ventricular and atrioventricular pacing on femoral artery (FIG. 6A) and pulmonary capillary wedge (PCW) pressures (FIG. 6B).
Figure 6A:
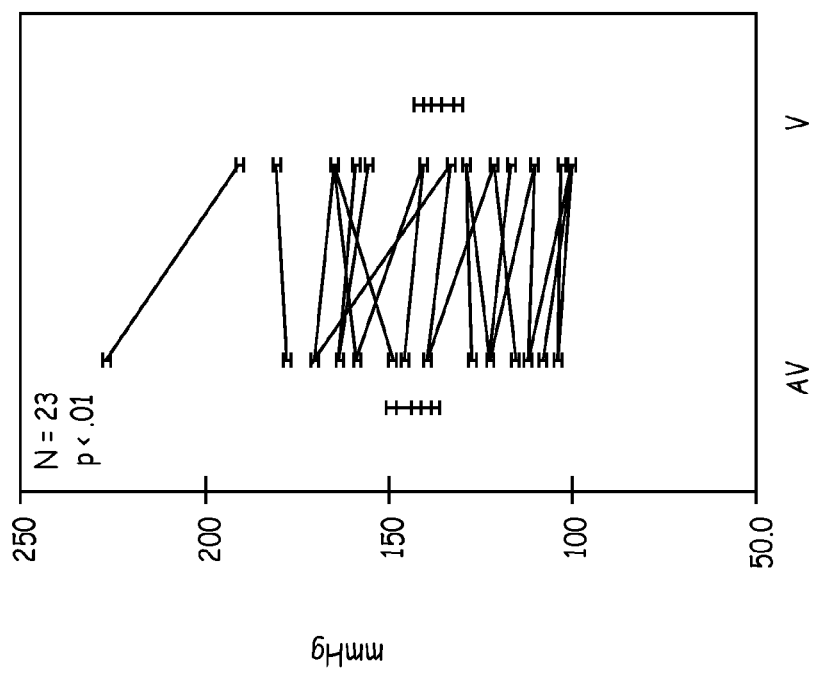

FIGS. 4 through 8 demonstrate exemplary effects of pacing on various cardiovascular pressures. FIG. 4 shows the effect of ventricular pacing on radial artery blood pressure of ventricular pacing at 80 BPM as compared to normal sinus rhythm (NSR). As shown in FIG. 4 the radial artery blood pressure is lower during the two intervals of ventricular pacing as compared to the two intervals of intrinsic ventricular activation. FIG. 5 shows the effect of ventricular and atrioventricular pacing on pulmonary capillary wedge (PCW) pressure. As shown in FIG. 5 the PCW diastolic pressure is moderately lower, and PCW systolic and pulse pressures are markedly lower, during AV sequential pacing as compared to ventricular-only pacing. FIG. 6 shows the effect of ventricular and atrioventricular pacing on femoral artery (left) and PCW (right) pressures. As shown in FIG. 6A the femoral artery pressure is significantly lower during ventricular-only pacing as compared to AV sequential pacing at 150 ms. As shown in FIG. 6B the PCW pressure is significantly higher during ventricular-only pacing as compared to AV sequential pacing at 150 ms.

Figure 7:
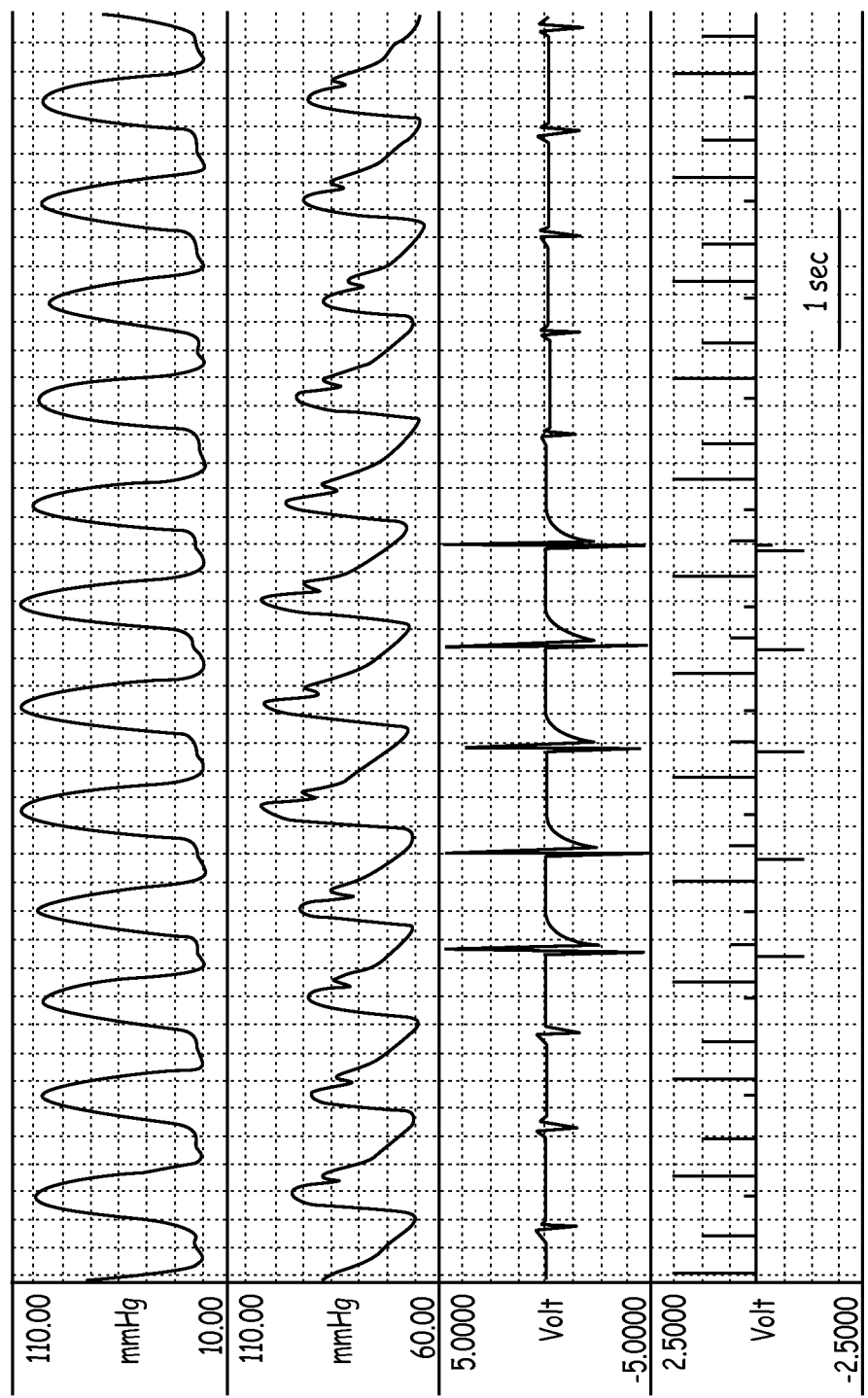
FIG. 7 is a graph showing the effect of LV pacing on left ventricular (first/top trace) and aortic (second trace) pressures.
Figure 8:
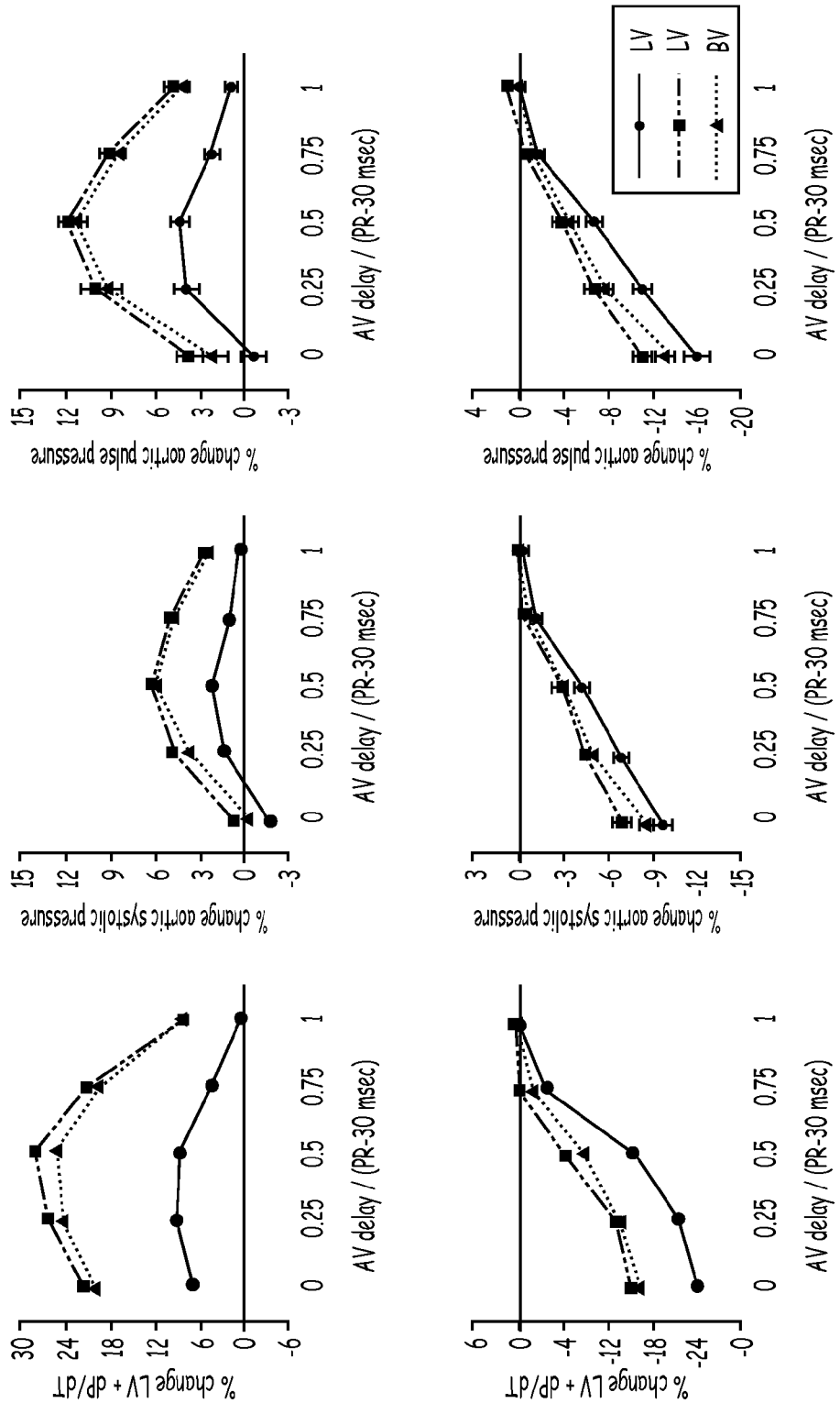
FIG. 8 is a graph showing the effect of pacing at different AV delays on systolic parameters.

FIGS. 7 and 8 were recorded during an investigation of Cardiac Resynchronization Therapy (CRT). FIG. 7 shows the effect on LV pacing on aortic and left ventricular pressures. Note the immediate change in LV pressure, LV positive dP/dt, and aortic pressure occur when pacing starts (indicated by larger potentials in electrogram); all changes are reversed within a few beats when pacing stops.

FIG. 8 shows the effect of pacing on hemodynamics as a function of 5 different AV delays on various systolic parameters for various chambers (RV, LV, BV). The top row of graphs represents acute responders to CRT; the lower row represents acute non-responders to CRT. The column at the left shows changes in the rate of change of left ventricular pressure (LV+dP/dt). The middle column shows changes in aortic systolic pressure. The column at the right shows changes in aortic pulse pressure.

FIG. 13 shows the hemodynamic effects of ventricular and atrioventricular pacing. Note that the diastolic, systolic and mean pulmonary artery (PA), mean right atrium (RA), left ventricular (LV) systolic, systolic femoral artery (FA) pressures are all significantly affected by the type of pacing.

Since cardiovascular pressure can vary depending upon the presence and type of cardiac pacing, knowledge of the existence or type of pacing may be helpful in analyzing and understanding cardiovascular pressure data. Further, therapy can be modified to improve the quality if one pacing configuration produces cardiovascular pressures more favorable to the patient's symptoms and clinical outcome. Therefore, in one embodiment, cardiovascular pressure data is classified according to one or more pacing parameters at the time the pressure is detected.

In one embodiment, cardiovascular pressure is classified strictly according to a classification parameter (e.g., cardiac cycle type). In another embodiment, cardiovascular pressure is classified using the majority cardiac cycle type to classify an entire measurement interval, but excluding cycles of a different type from summary calculations(s) (e.g., the mean). In another embodiment, cardiovascular pressure is classified using the majority cardiac cycle type to classify an entire measurement interval, and including cycles of a different type in summary calculation(s) (e.g., the mean). In yet another embodiment, cardiovascular pressure is classified using weights for each cardiac cycle type in summary calculation(s).

Display

Current systems providing chronic (e.g. ambulatory) cardiovascular pressure data do not classify pressure data according to the type of cardiac cycle. Thus the physician is unable to knowledgeably modify therapies to produce the type of cardiac cycle that will result in cardiovascular pressures most beneficial the patient. However, once classified according to the type of cardiac cycle, the cardiovascular pressure data may be displayed in various graphical forms. Displaying the data, as exemplified in FIGS. 9-12, would reveal the pressure and pressure differences among various types of cardiac cycles. Using this information the device can be programmed to produce the types of cardiac cycles most beneficial to the patient. Alternatively the data could be used by the implantable medical device to change the therapy of the device to produce the types of cardiac cycles most beneficial to the patient.

Examples of suitable display concepts are shown in FIGS. 9-12. However, the display possibilities are not limited to the concepts shown. Other display concepts are also possible.

Figure 9:
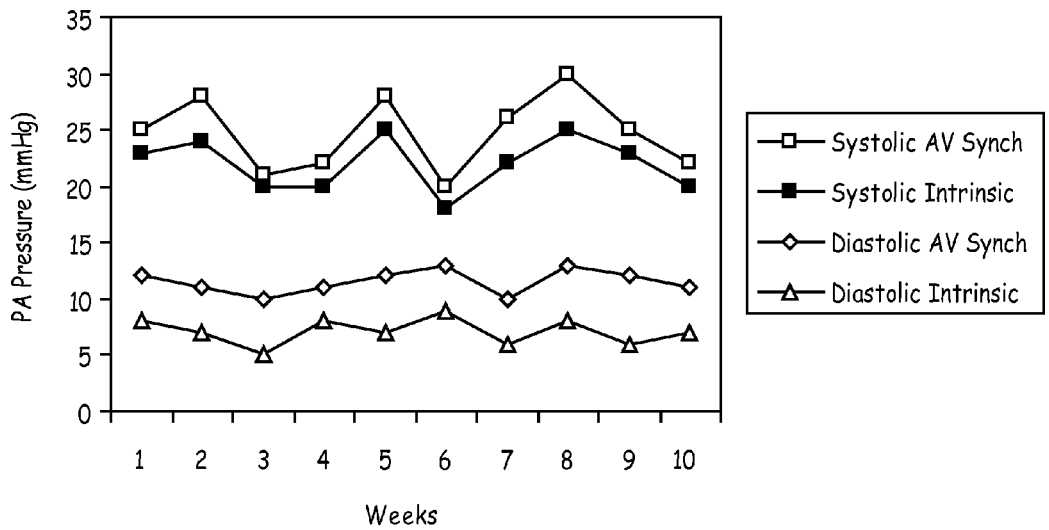
FIG. 9 is a graph depicting a time trend of pulmonary artery (PA) pressure for various cardiac cycle types.

FIG. 9 depicts a time trend of pulmonary artery (PA) pressure wherein multiple simultaneous PA pressure trends have been created. Two systolic and two diastolic trends were created. The diastolic and systolic trends were further separated according to whether the cardiac cycle was an intrinsic cycle or was a cycle wherein atrioventricular (AV) sequential pacing was delivered. As shown in the Figure, both the diastolic and systolic pressures were lower for intrinsic cardiac cycles as compared to cycles in which there was AV sequential pacing. In general, for most people, and in particular for heart failure patients, a lower PA pressure is desirable. Therefore, in one embodiment, this type of trend data could be used by the physician or other user to program the implantable medical device to increase the proportion of intrinsic cycles. In another embodiment an algorithm within the implantable medical device could adjust therapy to increase the proportion of intrinsic cycles.

Figure 10:
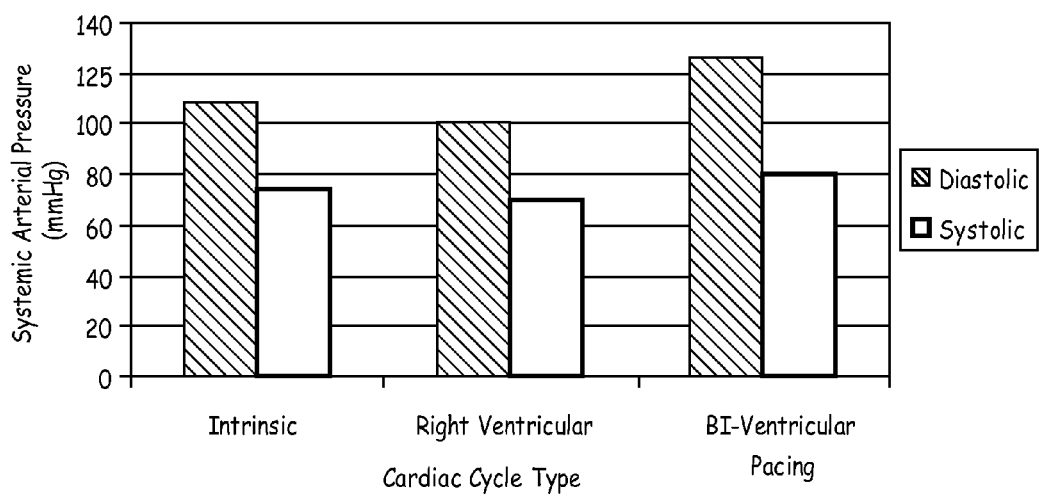
FIG. 10 is a graph depicting a bar chart of pulmonary artery (PA) pressure for various cardiac cycle types.

FIG. 10 depicts a bar chart of systemic arterial pressure wherein separate cardiac data data groups have been created according to the presence or absence of ventricular pacing and the site(s) of ventricular pacing. As shown in the Figure, both the diastolic and systolic pressures are higher for intrinsic cardiac cycles as compared to cycles in which there was pacing in only the right ventricle. Further, both the diastolic and systolic pressures are higher for cycles in which there was bi-ventricular pacing as compared to cycles in which there was pacing in only the right ventricle. For most people, lower systemic arterial pressures are desirable. However, this is not true for heart failure patients suffering from hypotension, a condition stemming from their weak heart. Therefore in one embodiment this type of histogram data could be used by the physician or other user to program an implantable medical device in a heart failure patient suffering from hypotension to increase the proportion of bi-ventricular pacing cycles to treat their hypotension. In another embodiment, an algorithm within the implantable medical device could use this data to adjust therapy to increase the proportion of bi-ventricular pacing cycles.

Figure 11:
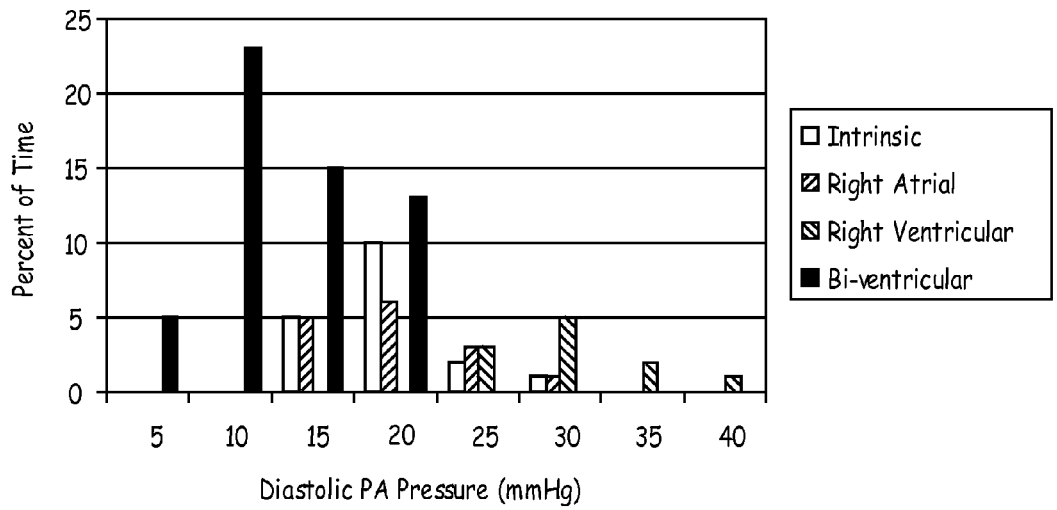
FIG. 11 is a histogram of pulmonary artery (PA) pressure for various cardiac cycle types.

FIG. 11 depicts a histogram of the diastolic pulmonary artery (PA) pressure wherein separate data bins have been created according to the presence or absence of pacing and the pacing site(s). As shown in the Figure, the diastolic PA pressure is highest for cardiac cycles in which there was pacing only in the right ventricle. The diastolic PA pressure for intrinsic cycles is similar to the diastolic PA pressure for cycles in which there was right atrial pacing. Also the diastolic PA pressure is lower for both intrinsic cycles and for cycles in which there was right atrial pacing as compared to cycles in which that were paced only in the right ventricle. Finally, cycles in which there was bi-ventricular pacing had the lowest diastolic PA pressure. Since heart failure patients generally benefit from lower diastolic PA pressures, in one embodiment, the histogram data depicted in FIG. 11 could be used by the physician or other user to program an implantable medical device to increase the proportion of bi-ventricular pacing cycles as compared to intrinsic cycles, right ventricular-only cycles and right atrial paced cycles. In another embodiment, an algorithm within the implantable medical device could use the data to adjust therapy to increase the proportion of bi-ventricular pacing cycles as compared to intrinsic cycles, right ventricular-only cycles and right atrial paced cycles.

Figure 12:
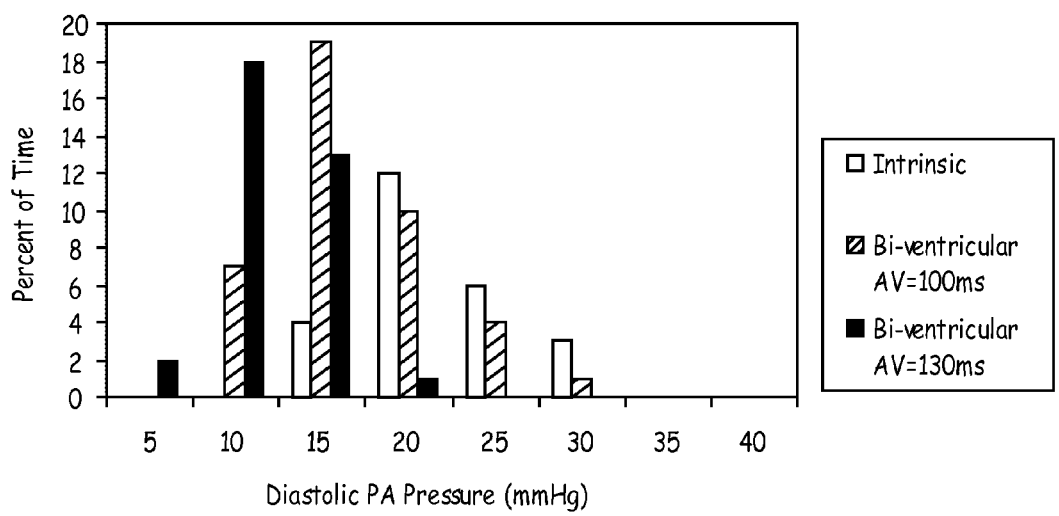
FIG. 12 is a histogram of pulmonary artery (PA) pressure for various cardiac cycle types, illustrating the difference between two atrioventricular (AV) delays.

FIG. 12 depicts a histogram of diastolic pulmonary artery (PA) pressure for various cardiac cycle types, illustrating the difference between intrinsic cycles and paced cycles. The paced cycles are further separated according to the atrioventricular (AV) delay used during pacing. As shown in the Figure, the diastolic PA pressure is highest for intrinsic cycles and is the lower for both paced cardiac cycle types with pacing at an AV delay of 130 ms producing the lowest PA diastolic pressure. Since heart failure patients generally benefit from lower diastolic PA pressures, in one embodiment, the histogram data depicted in FIG. 12 could be used by the physician or other user to program the atrioventricular (AV) delay of the implantable medical device (IMD) to 130 ms, thereby decreasing the diastolic pulmonary artery (PA) pressure. In another embodiment, an algorithm within the implantable medical device could use the data to adjust therapy to use an AV delay of 130 ms.

Pacing Therapy

In one embodiment, one or more functions relating to the programming of cardiac pacing therapy are modulated based on the characterization or classification of the pressure data. In one embodiment, modulating one or more functions of the implanted medical device includes modulating one or more pacing parameter values. As used herein, the term "pacing parameter" refers to one or more of many elements that govern the function and behavior of a pacemaker. Many pacing parameters are programmable and may include, for example, pacing mode, pacing rate, pacing site, a pulse waveform (e.g. pulse duration, pulse width, monophasic/biphasic), atrioventricular (AV) interval, biventricular delay, refractory periods, sensitivity of the sensing circuit, voltage amplitude, upper rate limit, lower rate limit, and hysteresis (the extension of the escape interval after a sensed intrinsic event). In one embodiment, the term "biventricular delay" refers to the interval between right ventricular and left ventricular pacing pulses delivered within the same cardiac cycle. In another embodiment, the term "biventricular delay" refers to the interval between a ventricular pacing pulse at a first site and a ventricular pacing pulse at a second site delivered within the same cardiac cycle, wherein the first and second sites are within the same ventricular chamber.

In one embodiment, modulating one or more functions of the implanted medical device includes modulating a pacing mode of the cardiac pacing therapy. As used herein, "pacing mode" refers to the manner in which a pacemaker provides rate and rhythm support to a patient. Pacing modes are described by the NASPE/BPEG Generic (NBG) Pacemaker Code, a five-letter designation that indicates the chamber(s) paced, the chamber(s) sensed, the mode of response to sensed events (e g, inhibited or triggered), programmability, and multisite pacing. Conventionally, only the first three positions (letters) of the NBG code are used to specify the pacing mode. The table below provides a summary of the NBG pacemaker code. See, Bernstein et al., The NASPE/BPEG Pacemaker Code for antibradyarrhythmia and adaptive-rate pacing and antitachyarrhythmia devices. *PACE*, 10:794-799, 1987. Although the type of cardiac cycle frequently refers to the pacing mode used in the cardiac cycle, intrinsic cardiac cycles (i.e., no pacing) can also be included as a type of cardiac cycle and is associated with the three letter code OOO.

As used herein, the term "atrial pacing" refers to electrical stimulation of the atrial myocardium, for example, to control bradycardia or tachycardia, including both synchronous and asynchronous pacing. As used herein, the term "synchronous pacing" refers to pacing in which information about a sensed activity in one or more cardiac chambers is used to determine the timing of impulse generation by the pacemaker. As used herein, the term "asynchronous pacing" refers to pacing in which impulse generation by the pacemaker occurs at a fixed rate, independent of underlying cardiac activity. In one embodiment, atrial pacing includes bi-atrial pacing. In one embodiment, atrial pacing includes atrial demand inhibited pacing (AAI). In another embodiment, atrial pacing includes atrial-inhibited rate-adaptive pacing (AAIR). In another embodiment, atrial pacing includes atrial demand triggered pacing (AAT). In another embodiment, atrial pacing includes atrial-triggered rate-adaptive pacing (AATR). In another embodiment, atrial pacing can include atrial asynchronous pacing (AOO).

As used herein, the term "ventricular pacing" refers to electrical stimulation of the lower chambers of the heart, the ventricles. Ventricular pacing can include right ventricular pacing, left ventricular pacing and bi-ventricular pacing. The term "biventricular pacing" refers to stimulation of both the right and left ventricle, in which stimulation may be simultaneous or there may be an offset (delay) with either left or right ventricular stimulation followed by stimulation in the other ventricle. Ventricular pacing includes both synchronous and asynchronous pacing. In one embodiment, ventricular pacing includes atrial synchronized ventricular inhibited pacing (VDD). In another embodiment, ventricular pacing includes VDD pacing with rate-adaptive capability (VDDR). In another embodiment, ventricular pacing includes ventricular asynchronous pacing (VOO). In another embodiment, ventricular pacing includes ventricular-demand pacing (VVI). In another embodiment, ventricular pacing includes ventricular demand inhibited pacing (VVIR). In another embodiment, ventricular pacing includes ventricular demand triggered pacing (VVT). Although not commonly used today, ventricular pacing can also include atrial-synchronized ventricular pacing (VAT).

As used herein, the term "atrioventricular pacing" or "dual chambered pacing" refers to a device that has the capability of

TABLE 1

The 1987 NASPE/BPEG Generic (NBG) Pacemaker Code

| | Position | | | | |
|---|---|---|---|---|---|
| | I | II | III | IV | V |
| | | | Category: | | |
| | Chamber(s) paced | Chamber(s) sensed | Response(s) to sensing | Programmability, rate modulation | Anti-tachyarrhythmia function(s) |
| | O = None | O = None | O = None | O = None | O = None |
| | A = Atrium | A = Atrium | T = Triggered | P = Simple programmable | P = Pacing (anti-tachyarrhythmia) |
| | V = Ventricle | V = Ventricle | I = Inhibited | M = Multi-programmable | S = Shock |
| | D = Dual (A + V) | D = Dual (A + V) | D = Dual (T + I) | C = Communicating | D = Dual (P + S) |
| | | | | R = Rate modulation | |
| Manufacturers' designation only: | S = Single (A or V) | S = Single (A or V) | ** | ** | ** |

** Note:
Positions I through III are used exclusively for antibradyarrhythmia function.

electrical stimulation of either or both atrial and ventricular chambers. Atrioventricular pacing can include synchronous and/or asynchronous pacing. Atrioventricular pacing can include sequential pacing in which atrial pacing is followed by a paced or sensed ventricular event. In one embodiment, atrioventricular pacing includes universal pacing (DDD). In another embodiment, atrioventricular pacing refers to a universal pacemaker that is responsive to the patient's respiratory rate and thus to exercise and metabolic needs (DDDR). In another embodiment, atrioventricular pacing refers to sequential dual-chamber inhibited pacing (DDI). In another embodiment, atrioventricular pacing refers to sequential dual-chamber inhibited pacing that is responsive to the patient's respiratory rate (DDIR). In another embodiment, atrioventricular pacing refers to atrioventricular sequential asynchronous pacing (DOO). In another embodiment, atrioventricular pacing refers to atrioventricular sequential ventricular-inhibited pacing (DVI). In another embodiment, atrioventricular pacing refers to atrioventricular sequential, ventricular-inhibited, rate-adaptive pacing (DVIR).

Another pacing parameter that can be modulated includes the cardiac pacing site. As used herein, the term "pacing site" refers to the location within one or more chambers of the patient's heart at which electrical stimulation of the cardiac tissue is applied. In one embodiment, the pacing site is broadly characterized, for example, atrial, ventricular and/or atrioventricular. In another embodiment, the pacing site is more specifically characterized, for example, bi-atrial, bi-ventricular, left ventricular, and/or right ventricular.

Typically, a patient paced according to NBG code VVI is paced at a single site within the right and/or left ventricle. However in another embodiment, a cardiac cycle can be classified based on pacing at multiple pacing sites within an individual chamber. For example, a cardiac cycle may be classified based on pacing at two sites on the left ventricular epicardium.

System

FIG. 1 is a schematic view of an implantable medical device 100 shown in conjunction with a heart 50. The device 100 generally includes a hermetically sealed housing 200 that encases the electronics for the device 100, a connection header 110, one or more leads 104, 106 and one or more electrodes 124, 134, 126, 136. The leads 104, 106 electrically couple a pulse generator 102, located within the housing 200, with the heart 50. Distal ends 114, 116 of the electrical stimulation leads 104, 106 have one or more electrodes 124, 134, 126, 136, which are disposed in operative relation to the patient's heart 50. The leads 104,106 can include one or more of the following electrodes: cardioversion/defibrillation electrodes, pacing electrodes and/or sense electrodes. Typically, the header 110 defines one or more apertures 111, 112 configured to receive a proximal end 144, 146 of a lead 104,106. The apertures 111, 112 include one or more electrical contacts (not shown) that extend from the header 110 to the internal circuitry (not shown). Typically, wires made from a conductive material pass from the pulse generator 102 within the housing 200 to one or more connector blocks (not shown) within the header 110.

When in use, the device 100 is implanted in the patient. In operation, the pulse generator 102 may generate pacing pulses and/or therapeutic shocks which are delivered from the header assembly 110 through the leads 104, 106 and to the heart 50. In many embodiments, the leads 104, 106 include a material that is electrically conductive in order to deliver the pacing pulses or therapeutic shocks.

Figure 2:
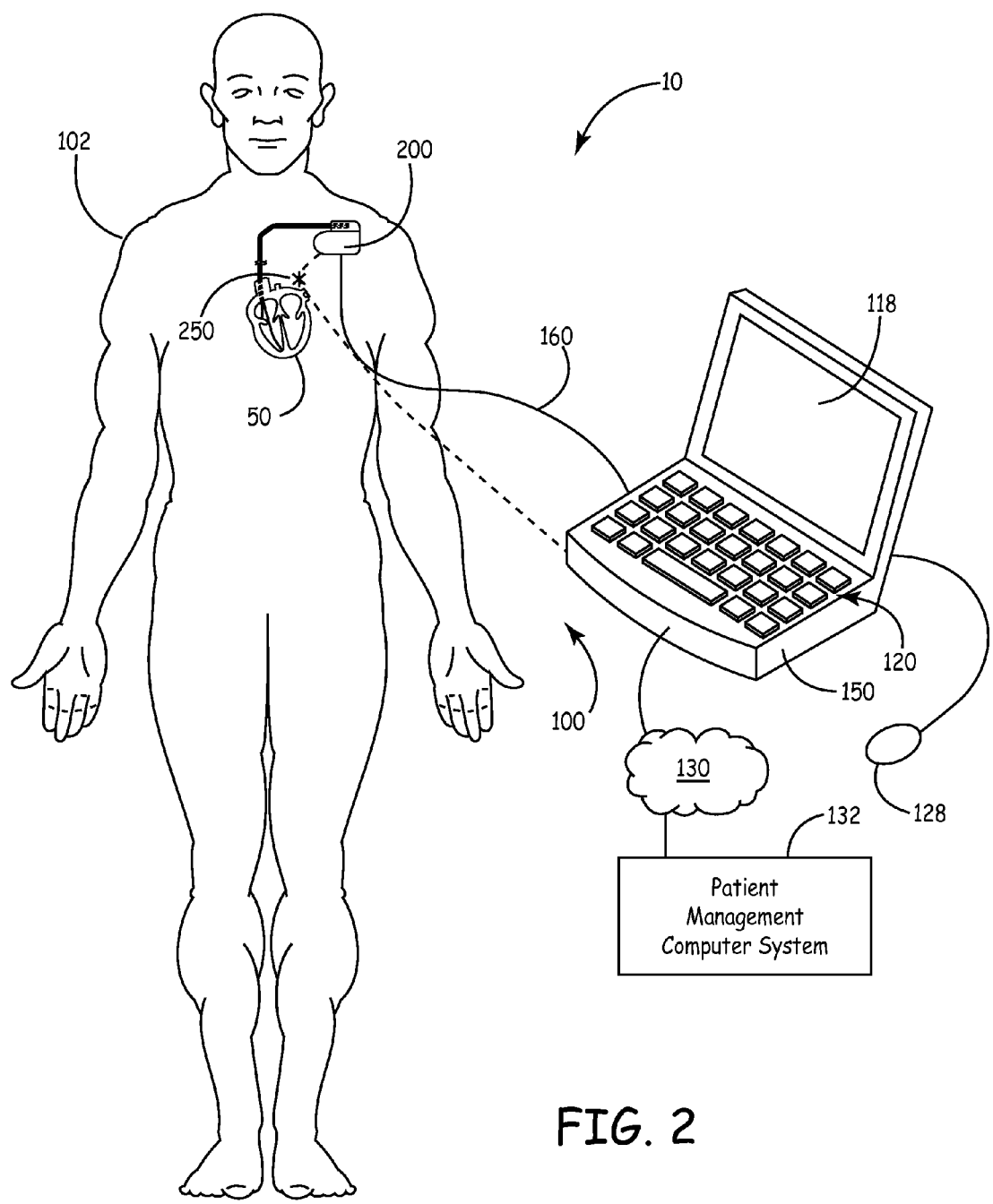
FIG. 2 is a schematic of a cardiac rhythm management system described herein.

FIG. 2 is a block diagram showing a system for collection, analysis and/or display of patient information retrieved from an implantable medical device. The system 10 includes an implantable medical device 100 that is configured for implantation within a patient 102. In one embodiment, the implantable medical device 100 includes a pacing functionality. The implantable medical device 100 can be of various types such as, for example, a pacemaker, a cardioverter-defibrillator, a cardiac resynchronization deivce, a heart rhythm monitoring device, or the like. In some embodiments, the implantable medical device 100 can include one or more leads disposed in or near the patient's heart 50.

In one embodiment, the implantable medical device 100 is in communication with an external device 150. In one embodiment, communication between the implantable medical device 100 and the external device 150 can be via inductive communication through a wand held on the outside of the patient 102 near the implantable medical device 100. In other embodiments, communication can be carried out via radiofrequency transmission, acoustically, or the like. The implantable medical device 100 can be configured to store data over a period of time, and periodically communicate with the external device 150 to transmit some or all of the stored data. The external medical device 150 can include a communication circuit configured to receive information from the implantable medical device. In some examples, the information is received into a memory.

The system 10 can include one or more sensors 250. In one embodiment, the system 10 includes one or more implantable sensors 250 used to gather information (or data) about the patient 102. In one embodiment, the system 10 includes a blood pressure sensor, an activity level sensor, a respiration sensor, an impendence sensor or other suitable sensor. In one embodiment, the system 10 includes one or more cardiovascular pressure sensors. In another embodiment, the system 10 includes one or more pulmonary artery pressure sensors.

In one embodiment, the system 10 includes one or more sensors 250 operably connected to the implantable medical device 100 and configured to communicate or transmit a sensor signal associated with one or more physiologic conditions of a subject to a database capable of storing patient information. In one embodiment, one or more sensors 250 are configured to communicate or transmit a sensor signal to an implantable medical device 100, an external device 150, or both. In one embodiment, one or more sensors 250 are capable of generating a signal indicative of one or more characteristics of a cardiac cycle of the patient's heart. In another embodiment, one or more sensors 250 are capable of generating a signal indicative of a cardiovascular pressure of the patient. In another embodiment, the system 10 includes one or more internal or implanted sensors 250. In one embodiment, one or more sensors 250 are "hard wired" or physically attached to the implantable medical device 100. For example, the sensor 250 can be communicably attached to the implantable medical device by one or more leads. In another embodiment, one or more sensors 250 communicate with the implantable medical device 100, an external device 150, or both wirelessly, for example, by telemetry. In one embodiment, the system 10 includes one or more external sensors 250 capable of producing an external sensor signal associated with one or more physiologic conditions of a patient. The external sensor 250 may be communicatively coupled to the implantable medical device 100, the external device 150, or both. In one embodiment, the external sensor is communicatively coupled to the implantable medical device 100, the external medical device 150, or both wirelessly. In another embodiment, the external sensor 250 is communicatively coupled to an external device 150 via a Universal Serial Bus (USB) or a serial channel.

The external device 150 can be for example, a programmer, a programmer/recorder/monitor device, a computer, a patient management system, a personal digital assistant (PDA), or the like. As used herein, the term programmer refers to a device that programs implanted devices, records data from implanted devices, and allows monitoring of implanted devices. Examples of programmer/recorder/monitor devices include the Model 3120 Programmer, available from Boston Scientific Corporation, Natick, Mass. The external device 150 can include a user input device, such as a keyboard 120 and/or a mouse 128. The external interface system 150 can include a video output channel and video output device, such as a video display 118 for displaying video output. The displayed video output can include a user interface screen. In addition, the video display 118 can also be equipped with a touch screen, making it into a user input device as well.

The external device 150 can display real-time data and/or stored data graphically, such as in charts or graphs, and textually through the user interface screen. In addition, the external device 150 can present textual information to a user along with several response options. The external device 150 can also input and store a user's response to a question, and can store a user's text response in some embodiments.

In one embodiment, the external device 150, which can also be referred to as a user interface, is in communication with a patient management computer system 132. The communication link between the user interface 150 and the patient management computer system 132 may be via phone lines, the Internet 130, or any other data connection. The user interface 150 can also be used when it is not in communication with a device, but is only in communication with the patient management computer system 132.

In one embodiment, the external device 150 is capable of changing one or more operational parameters of the implantable medical device 100, and is therefore referred to as a programmer. Typically, programmers are used to interface with implantable medical devices 100 in a clinic or hospital setting. In this context, the user of the external interface device is a physician or trained technician.

Figure 3:
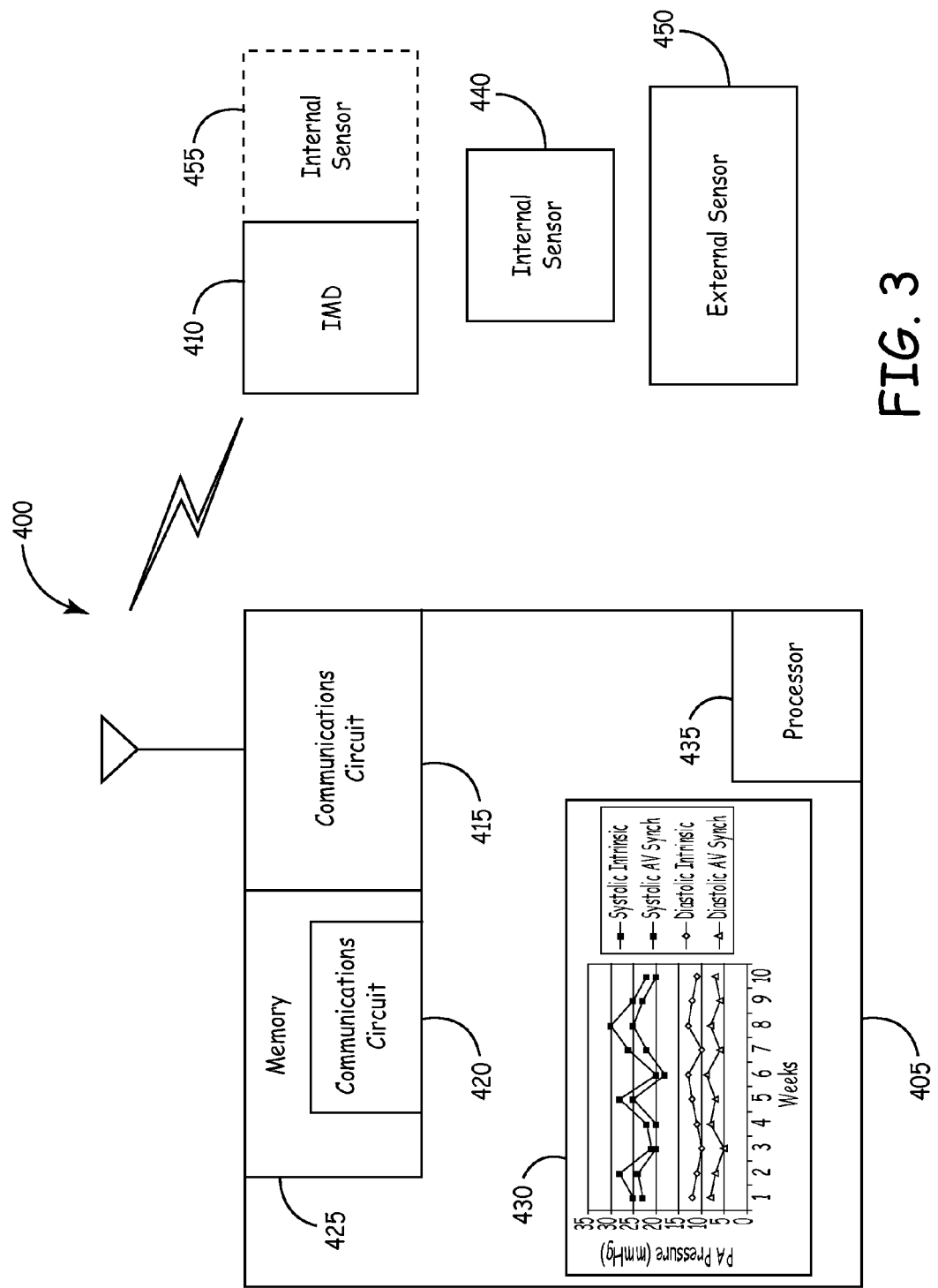
FIG. 3 is a schematic of a system configured to monitor cardiovascular pressure of a patient.

FIG. 3 is a block diagram of a system 400 configured to monitor one or more physiologic conditions of a patient. As used herein, the term "physiologic condition" of a patient refers to one or more mechanical, physical or biochemical functions of a patient. Examples of physiologic conditions that may be monitored include, but are not limited to, cardiovascular pressure, heart rate, respiratory rate, cardiac cycle, movement, temperature, impedance, posture, heart sound, respiratory sound, blood analyte (e.g. electrolyte, neuro-hormone, hematocrit). Physiologic sensors include, but are note limited to a subcutaneous electrogram sensor, pressure sensor, an accelerometer, a temperature sensor, a chemical sensor, an acoustic sensor, and an impedance sensor. Other sensors include sleep sensor, functional capacity indicator, autonomic tone indicator, sleep quality indicator, cough indicator, anxiety indicator, and cardiovascular wellness indicator for calculating a quality of life indicator quantifying a patient's overall health and well-being. Additional sensor readings that can be included are from a thermometer, a sphygmomanometer or other external devices.

In the embodiment shown, the system 400 includes an external medical device 405 that is configured to communicate with an implantable medical device 410. In one embodiment, the system 400 includes one or more internal or external sensors 440, 450, 455 configured to monitor one or more physiologic conditions of the patient. In one embodiment, the system 400 includes multiple sensors, or several devices 100 that are configured to monitor different sites within a patient's body. In one embodiment, one or more sensors are configured to monitor one or more characteristics of a cardiac cycle. In another embodiment, one or more sensors are configured to monitor a cardiovascular pressure. In one embodiment, one or more sensors 440, 450, 455 are configured to transmit signals to a database and/or processor capable of storing and/or analyzing patient physiologic information 420. In one embodiment, the external device 405 includes memory components 425, a processor 435, or both. In another embodiment, the implantable medical device 410 includes a database, a processor, or both.

In one embodiment, the sensor integrated with or physically attached to the implantable medical device. In another embodiment, the sensor is a stand alone sensor that is capable of being operated independently of the implantable medical device 410. There are many options for equipment for the transmission of data from a sensor 440, 450, 455 to an implantable medical device 410, an external medical device 405, or both. For example, the implantable medical device 410 or sensor 440, 450, 455 can include a telemetry transmitter and receiver for communicating information to an external medical device (or the implantable medical device, in the case of a sensor) and for receiving commands or other information from the external medical device. In one embodiment, the implantable medical device 410 includes an antenna connected to the circuitry for purposes of transmitting analog and/or digital data between antenna and the external medical device 405 through an RF transmitter/receiver (RF TX/RX) unit. In another embodiment, the external sensor 450 is communicatively coupled to the external medical device 405 by a Universal Serial Bus (USB) or a serial channel. In another embodiment, the external sensor 450 is communicatively coupled to the implantable medical device 410, the external medical device 405, or both wirelessly. In one embodiment, the external medical device 405 includes a communication circuit 415 that is configured to receive information associated with one or more physiologic conditions of a patient. In one embodiment, the physiologic information 420 is received into a memory 425.

In one embodiment, the external medical device 405 includes a display 430. In one embodiment, the external medical device 405 receives both cardiovascular pressure information and information associated with a characteristic of a cardiac cycle of the patient's heart. In one embodiment, the external medical device 405 is configured to display cardiovascular pressure information classified based on one or more characteristics of a cardiac cycle of the patient at the time the cardiovascular pressure is measured. In another embodiment, the external medical device 405 is configured to display cardiovascular pressure information based on whether or not the patient's heart was paced at the time the cardiovascular pressure was measured.

In one embodiment, the external medical device 405 includes a programming device for the implantable medical device 410. In one embodiment, the external medical device 405 is communicatively coupled to a communication network, such as the internet or a mobile telephone network. In one embodiment, the external medical device 405 communicates with the implantable medical device 410 using a third device, such as a repeater. Similar technology can be used to transfer programming commands to the implanted device during and after implantation.

Figure 15:
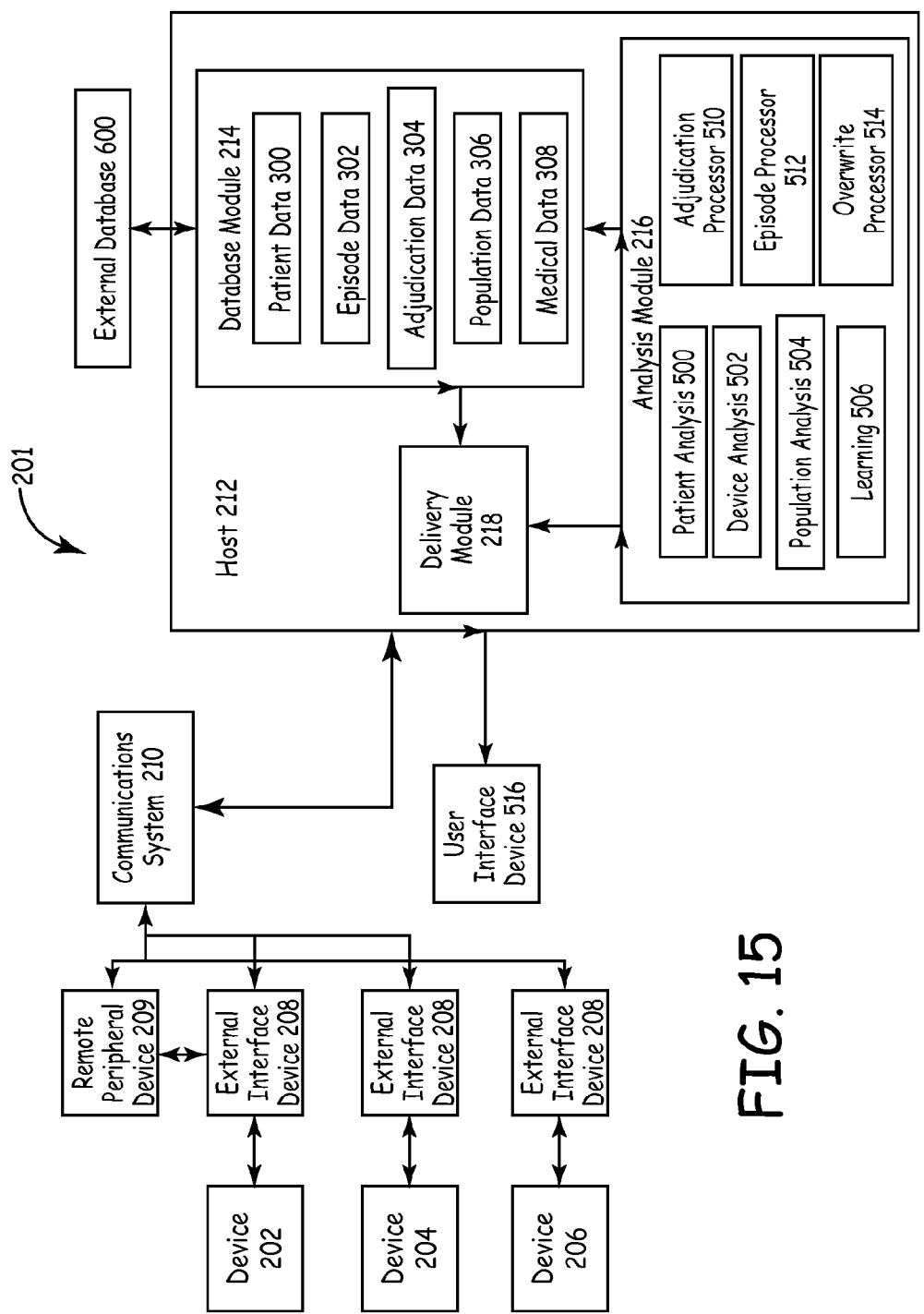
FIG. 15 is a schematic illustration of a patient management system consistent with at least one embodiment of the invention.

FIG. 15 is a schematic illustration of a patient management system consistent with at least one embodiment of the invention. The patient management system is capable of generating an episode database and supporting a training module. Patient management system 201 generally includes one or more devices 202, 204, and 206, one or more external interface devices 208, a communication system 210, one or more remote peripheral devices 209, and a host 212.

Each component of the patient management system 201 can communicate using the communication system 210. Some components may also communicate directly with one another. The various components of the example patient management system 201 illustrated herein are described below.

Data-generating devices 202, 204, and 206 can be implantable devices or external devices that may provide one or more of the following functions with respect to a patient: (1) sensing, (2) data analysis, and (3) therapy. For example, in one embodiment, devices 202, 204, and 206 are either implanted or external devices used to measure a variety of physiological, subjective, and environmental conditions of a patient using electrical, mechanical, and/or chemical means. The devices 202, 204, and 206 can be configured to automatically gather data or can require manual intervention by the patient or another person. The devices 202, 204, and 206 can be configured to store data related to the physiological and/or subjective measurements and/or transmit the data to the communication system 210 using a variety of methods, described in detail below. Although three devices 202, 204, and 206 are illustrated in the example embodiment shown, many more devices can be coupled to the patient management system. In one embodiment, each of the devices 202, 204 and 206 is serving a different patient. In one embodiment, two or more devices are serving a single patient.

The devices 202, 204, and 206 can be configured to analyze the measured data and act upon the analyzed data. For example, the devices 202, 204, and 206 can be configured to modify therapy or provide an alarm based on the analysis of the data.

In one embodiment, devices 202, 204, and 206 provide therapy. Therapy can be provided automatically or in response to an external communication. Devices 202, 204, and 206 are programmable in that the characteristics of their sensing, therapy (e.g., duration and interval), or communication can be altered by communication between the devices 202, 204, and 206 and other components of the patient management system 201. Devices 202, 204, and 206 can also perform self-checks or be interrogated by the communication system 210 to verify that the devices are functioning properly. Examples of different embodiments of the devices 202, 204, and 206 are provided herein.

Devices implanted within the body have the ability to sense and communicate as well as to provide therapy. Implantable devices can provide direct measurement of characteristics of the body, including, without limitation, electrical cardiac activity (e.g., a pacemaker, cardiac resynchronization management device, defibrillator, etc.), physical motion, temperature, heart rate, activity, blood pressure, breathing patterns, ejection fractions, blood viscosity, blood chemistry, blood glucose levels, and other patient-specific clinical physiological parameters, while minimizing the need for patient compliance. Derived measurements can also be determined from the implantable device sensors (e.g., a sleep sensor, functional capacity indicator, autonomic tone indicator, sleep quality indicator, cough indicator, anxiety indicator, and cardiovascular wellness indicator for calculating a quality of life indicator quantifying a patient's overall health and well-being).

Devices 202, 204, and 206 can also be external devices, or devices that are not implanted in the human body, that are used to measure physiological data (e.g., a thermometer, sphygmomanometer, or external devices used to measure blood characteristics, body weight, physical strength, mental acuity, diet, heart characteristics, and relative geographic position).

The patient management system 201 may also include one or more remote peripheral devices 209 (e.g., cellular telephones, pagers, PDA devices, facsimiles, remote computers, printers, video and/or audio devices) that use wired or wireless technologies to communicate with the communication system 210 and/or the host 212.

Communications system 210 may use one or more methods to facilitate communication between external interface device 208, remote peripheral devices 209 and host 212. Communications system 210 may use a wired, wireless or a combination of wired and wireless communication modes. Communications system 210 may use the Internet, a local area network, a non-Internet wide area network, or a combination of these or other networks.

The example database module 214 includes a patient database 300, an episode database 302, an adjudication database 304, a population database 306, and a medical database 308, all of which are described further below. The patient database 300 includes patient specific data, including data acquired by the devices 202, 204, and 206, as well as a patient's medical records and historical information. The population database 306 includes non-patient specific data, such as data relating to other patients and population trends. The example medical database 308 includes clinical data relating to the treatment of diseases, such as historical trend data for multiple patients in the form of a record of progression of their disease(s) along with markers of key events.

The episode database 302 has episode data regarding a plurality of different arrhythmia episodes generated from those of devices 202, 204, and 206 that provide arrhythmia episode data. The adjudication database 304 includes adjudication conclusions associated with the episode data such as arrhythmia episodes. The adjudication database 304 and the episode database 302 can actually be a single database with shared data that is used as either episode data or adjudication data depending on the particular data set being presented to the user.

Information can also be provided from an external source, such as external database 600. For example, the external database 600 includes external medical records maintained by a third party, such as drug prescription records maintained by a pharmacy, providing information regarding the type of drugs that have been prescribed for a patient or, in another example, authorization data from patient groups that have authorized users to view arrhythmia episode data.

The example analysis module 216 includes a patient analysis module 500, device analysis module 502, population analysis module 504, and a learning module 506. Patient analysis module 500 may utilize information collected by the patient management system 201, as well as information for other relevant sources, to analyze data related to a patient and provide timely and predictive assessments of the patient's well-being. Device analysis module 502 analyzes data from the devices 202, 204, and 206 and external interface devices 208 to predict and determine device issues or failures. Population analysis module 504 uses the data collected in the database module 214 to manage the health of a population. Learning module 506 analyzes the data provided from the various information sources, including the data collected by the patient system 200 and external information sources, and may be implemented via a neural network (or equivalent) system to perform, for example, probabilistic calculations.

The analysis module 216 further includes an adjudication processor 510, and episode processor 512 and an overwrite processor 514. In one embodiment, the adjudication processor is operatively connected to at least the episode database 302 and is configured to receive as input episode data regarding one of the different arrhythmia episodes. The adjudication processor uses an automated method or algorithm to generate characterization data about the arrhythmia episode. The characterization data, including an arrhythmia classification for each arrhythmia episode that is analyzed, is stored in the adjudication database 304.

The episode processor 512 performs processing of the adjudication database such as in order to provide reports, patient alerts, or programming recommendations. The overwrite processor 514 can analyze data provided from the episode database 302, the adjudication database 304, and other portions of the patient management system 201 to determine what particular portion of episode data for one of the arrhythmia episodes from the episode database should be displayed to a user. Overwrite processor 514 can, through the delivery module 218 described below, provide the means for graphically displaying a portion of data selected from arrhythmia episode data related to an arrhythmia episode of a patient, such as data generated by a data-generating device and stored in the episode database.

Overwrite processor 514 also requests from a user any changes in the characterization data determined by the adjudication processor, and can articulate the request for user input characterizing an arrhythmia episode. The request may be a direct question to a user, a series of choices provided to the user, or simply a blank space on the user interface configured to accommodate the user input. The overwrite processor 514 may also store the overwrite history for individual users.

One or more portions of the analysis module 216, such as the adjudication processor 510 and episode processor 512, may be located remotely from other parts of the patient management system 201.

Delivery module 218 coordinates the delivery of reports, patient alerts or programming recommendations based on the analysis performed by the host 212. For example, based on the data collected from the devices and analyzed by the host 212, the delivery module 218 can deliver information to the caregiver, user, or to the patient using, for example, a display provided on the external interface device 208. A user interface device 516 that is independent of a data-generating device may also be used to deliver information. The external interface device 208 and user interface device 516 are also configured, according to multiple embodiments, to display a report, alert, or programming recommendation, receive overwrite information from a user, and receive other data from the user. Displayed data, as described above, can be determined by the episode processor 512, overwrite processor 514 and delivery module 218.

External interface devices 208 to display information, such as programmer/recorder/monitors, can include components common to many computing devices. User interface devices 516 to display and received information from users can also include components common to many computing devices.

Figure 16:
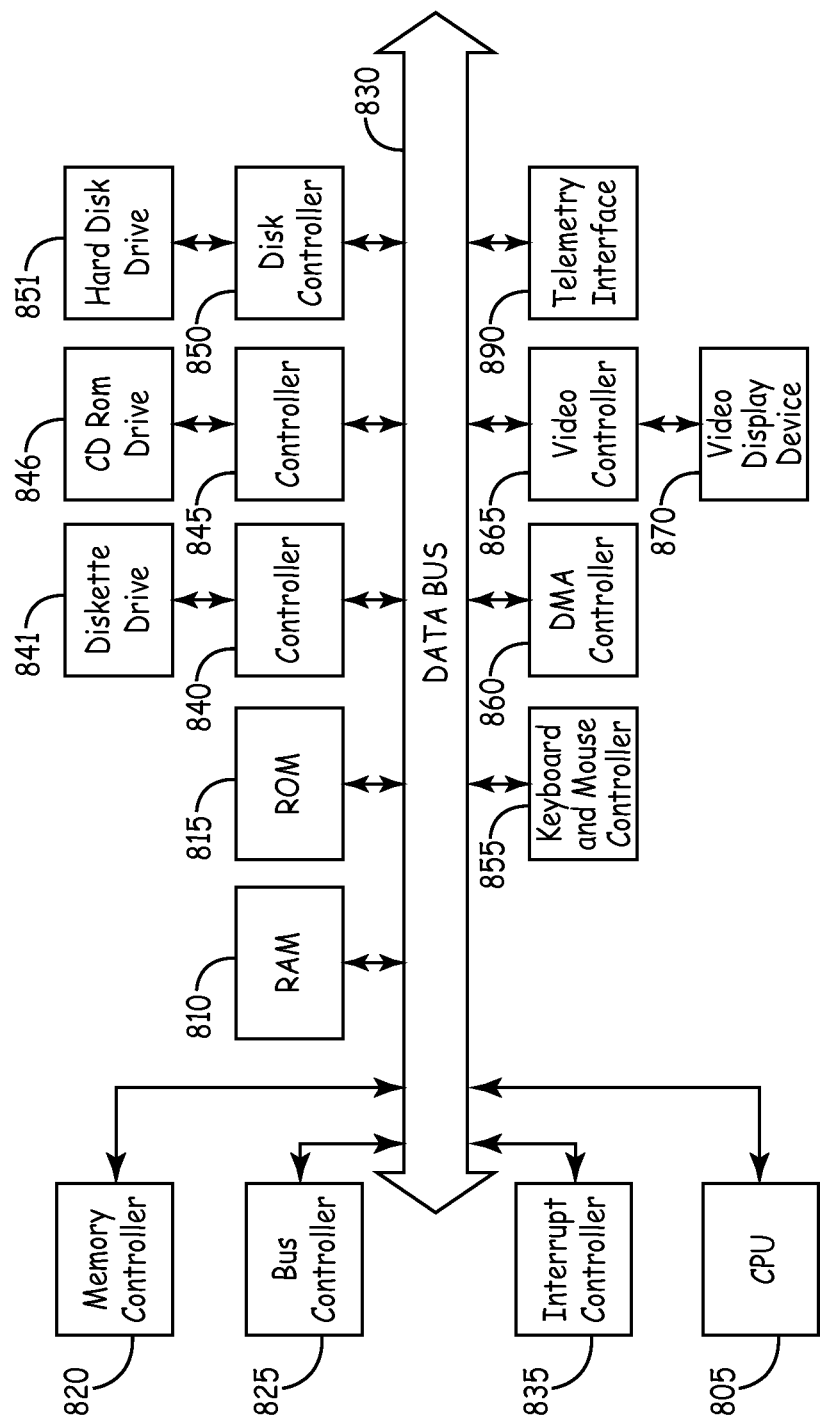
FIG. 16 is a schematic diagram of an implementation of the components of an external interface device such as a programmer, in accordance with various embodiments.

Referring now to FIG. 16, a diagram of various components is shown in accordance with some embodiments of the invention. However, it is not required that an external interface device have all of the components illustrated in FIG. 16.

In one embodiment, the external interface device includes a central processing unit (CPU) 805 or processor, which may include a conventional microprocessor, random access memory (RAM) 810 for temporary storage of information, and read only memory (ROM) 815 for permanent storage of information. A memory controller 820 is provided for controlling system RAM 810. A bus controller 825 is provided for controlling data bus 830, and an interrupt controller 835 is used for receiving and processing various interrupt signals from the other system components.

Mass storage can be provided by diskette drive 841, which is connected to bus 830 by controller 840, CD-ROM drive 846, which is connected to bus 830 by controller 845, and hard disk drive 851, which is connected to bus 830 by controller 850. User input to the programmer system may be provided by a number of devices. For example, a keyboard and mouse can connected to bus 830 by keyboard and mouse controller 855. DMA controller 860 is provided for performing direct memory access to system RAM 810. A visual display is generated by a video controller 865 or video output, which controls video display 870. The external system can also include a telemetry interface 890 or telemetry circuit which allows the external system to interface and exchange data with an implantable medical device. It will be appreciated that some embodiments may lack various elements illustrated in FIG. 16.

Figure 17:
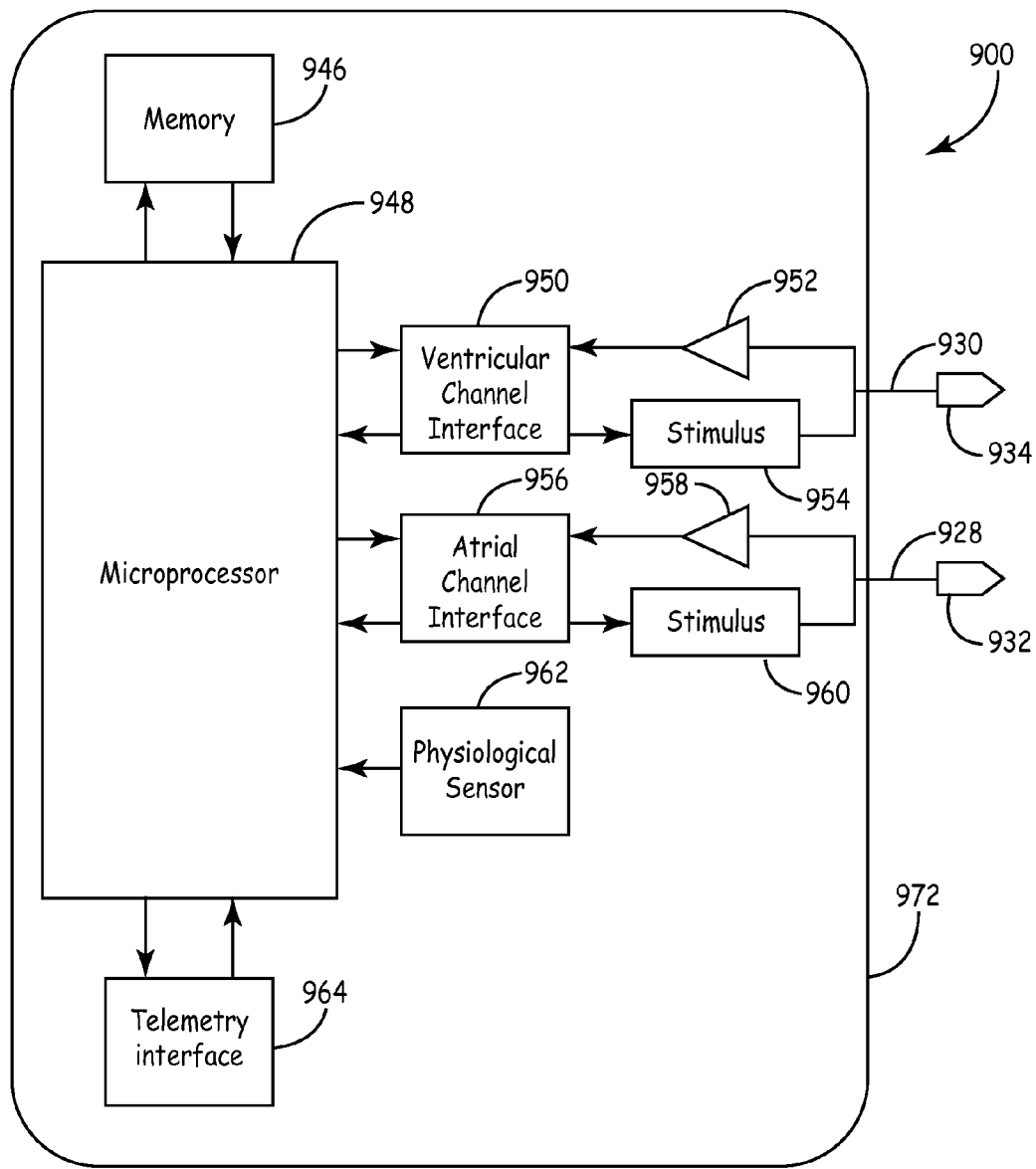
FIG. 17 is a schematic view of components of one example of a data-generating device in accordance with an embodiment of the invention.

Referring now to FIG. 17, some components of an exemplary implantable system 900 are schematically illustrated. The implantable medical system 900 can include an implantable medical device 972 coupled to one or more stimulation leads 930 and 928. The implantable device 972 can also include one or more physiological sensors 962, or other sensors, such as a pressure sensor, impedance sensor and others.

The implantable device can include a microprocessor 948 (or processor) that communicates with a memory 946 via a bidirectional data bus. The memory 946 typically comprises ROM or RAM for program storage and RAM for data storage. The implantable device can be configured to execute various operations such as processing of signals and execution of methods as described herein. A telemetry interface 964 is also provided for communicating with an external unit, such as a programmer device or a patient management system.

The implantable device can include ventricular sensing and pacing channels comprising sensing amplifier 952, output circuit 954, and a ventricular channel interface 950 which communicates bidirectionally with a port of microprocessor 948. The ventricular sensing and pacing channel can be in communication with stimulation lead 930 and electrode 934. The implantable device can include atrial sensing and pacing channels comprising sensing amplifier 958, output circuit 960, and an atrial channel interface 956 which communicates bidirectionally with a port of microprocessor 948. The atrial sensing and pacing channel can be in communication with stimulation lead 928 and electrode 932. For each channel, the same lead and electrode can be used for both sensing and pacing. The channel interfaces 950 and 956 can include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers.

An implantable medical device as described herein may include one or more of the features, structures, methods, or combinations thereof described herein. It is intended that an implantable medical device, as described herein, need not include all of the features described herein, but may be implemented to include one or more selected features that may provide one or more unique structures or functionality. Such a device may be implemented to provide a variety of therapeutic or diagnostic functions.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. It should be readily apparent that any one or more of the design features described herein may be used in any combination with any particular configuration. With use of the metal injection molding process, such design features can be incorporated without substantial additional manufacturing costs. That the number of combinations are too numerous to describe, and the present invention is not limited by or to any particular illustrative combination described herein. The scope of the present subject matter should be determined with reference to the appended claims, along with the full scope of equivalents to which such claims are entitled.

What is claimed is:

1. A system for collection and display of a cardiovascular pressure of a patient, wherein the patient has an implanted medical device capable of providing a stimulus to the patient's heart, the system comprising:
   (a) one or more cardiac cycle sensors capable of generating a first signal indicative of a characteristic of a cardiac cycle of the patient's heart;
   (b) one or more pressure sensors capable of generating a second signal indicative of a cardiovascular pressure of the patient;
   (c) one or more transmitters configured to transmit the first and second signal to a database capable of storing patient information in the form of cardiac cycle data and pressure data;
   (d) a processor configured to classify the cardiovascular pressure based on the cardiac cycle data, wherein the cardiac cycle data includes whether the cardiovascular pressure is determined during a cycle in which a stimulus was delivered to the patient's heart by the implantable medical device, whether the cardiac cycle is intrinsic at the time that the cardiovascular pressure is determined, what type of stimulus was applied that could affect the determined cardiovascular pressure or a combination thereof; and
   (e) a display showing the classification of the cardiovascular pressure.

2. The system of claim 1, wherein the cardiac cycle sensor is configured to be implanted within the patient.

3. The system of claim 1, wherein the cardiac cycle sensor is configured to be located external to the patient.

4. The system of claim 1, wherein cardiovascular pressure comprises pulmonary artery pressure.

5. The system of claim 1, wherein one or more cardiovascular pressure sensors are configured to be implanted within the patient.

6. The system of claim 1, wherein one or more cardiovascular pressure sensors are configured to be located external to the patient.

7. The system of claim 4, wherein cardiovascular pressure comprises intravascular pressure.

8. The system of claim 1, wherein cardiovascular pressure comprises an intracardiac pressure.

9. The system of claim 1, wherein the system further comprises a hemodynamic sensor.

10. The system of claim 1, wherein pressure comprises at least one of a diastolic pressure, a systolic pressure, a mean pressure, a pulse pressure, an end expiratory diastolic pressure, an end expiratory systolic pressure, a rate of change of a pressure, and a mean pressure.

11. The system of claim 1, wherein the characteristic of a cardiac cycle comprises at least one of systole, diastole, and an intervening phase.

12. The system of claim 1, wherein the pressure sensor is at least one of a direct pressure sensor and an indirect pressure sensor.

13. The system of claim 1, wherein the display comprises at least one of a time trend, a bar chart and a histogram.

14. The system of claim 1, wherein the system further comprises at least one of a subcutaneous electrogram sensor, an acceleration sensor, a temperature sensor, a chemical sensor, an acoustic sensor, and an impedance sensor.

15. The system of claim 1, wherein the system further comprises a physiological sensor wherein the sensor is configured to measure at least one of a heart rate, a respiratory rate, a cardiac cycle, a movement, a temperature, an impedance, a posture, a heart sound, a respiratory sound, a blood analyte.

16. The system of claim 1, wherein the implantable medical device is selected from pacemakers, implantable cardioverter defibrillators (ICDs), and cardiac resynchronization therapy (CRT) devices.

* * * * *